(12) United States Patent
Bartholomeusz et al.

(10) Patent No.: US 7,887,813 B2
(45) Date of Patent: Feb. 15, 2011

(54) VARIANTS OF HEPATITIS B VIRUS WITH RESISTANCE TO ANTI-VIRAL NUCLEOSIDE AGENTS AND APPLICATIONS THEREOF

(75) Inventors: Angeline Ingrid Bartholomeusz, Carnegie (AU); Stephen Locarnini, Balaclava (AU); Anna Ayres, Brunswick West (AU); Margaret Littlejohn, Coburg (AU); Paul Desmond, Albert Park (AU); Peter William Angus, East Ivanhoe (AU)

(73) Assignees: Melbourne Health, Victoria (AU); St. Vincent's Hospital Melbourne, Victoria (AU); Austin Health, Victoria (AU)

(*) Notice: Subject to any disclaimer, the term of this patent is extended or adjusted under 35 U.S.C. 154(b) by 207 days.

(21) Appl. No.: 11/932,410

(22) Filed: Oct. 31, 2007

(65) Prior Publication Data

US 2008/0176218 A1    Jul. 24, 2008

Related U.S. Application Data

(63) Continuation of application No. 11/911,097, filed as application No. PCT/AU2006/000450 on Apr. 4, 2006.

(30) Foreign Application Priority Data

| | | |
|---|---|---|
| Apr. 8, 2005 | (AU) | 2005901757 |
| Jul. 26, 2005 | (AU) | 2005903972 |

(51) Int. Cl.
A61K 39/29    (2006.01)
A61K 39/38    (2006.01)
C12Q 1/70     (2006.01)

(52) U.S. Cl. .................. 424/227.1; 435/5; 435/6; 435/235.1; 424/184.1

(58) Field of Classification Search .............. None
See application file for complete search history.

(56) References Cited

PUBLICATIONS

Chotiyaputta W. "Hepatitis B virus variants." Nat Rev Gastroenterol Hepatol. Aug. 2009;6(8):453-62.*
Villeneuve J-P. et al. "Selection of a hepatitis B virus strain resistant to adefovir in a liver transplantation pateint" J. of Hepatology, 39:1085-1089, 2003.*

* cited by examiner

*Primary Examiner*—Bo Peng
(74) *Attorney, Agent, or Firm*—Baker Botts L.L.P.

(57) ABSTRACT

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

3 Claims, 12 Drawing Sheets

CAAGCGCCAGTCAGGAAGGCAGCCTACCCCGCTGTCTCCACCTTTGAGAAACACG
CATCCTCAGGCCACGCAGTGGAACACCACAACCTTCCACCAAACTCTGCAAGATC
CCAGAGTGAAAGGCCTGTATTTCCCTGCTGGTGGCTCCAGTTCAGGAACAGTAAA
CCCTGTTCCGACTACTGCCTCTCCCTTATCGTCAATCTTCTCGAGGATTGGGGACC
CTGCACTGAACATGGAGAACATCACATCAGGACTCCTAGGACCCCTTCTCGTGTT
ACAGGCGGGGTTTTCTTGTTGACAAAAATCCTCACAATACCGCAGAGTCTAGAC
TCGTGGTGGACTTCTCTCAATTTTCTAGGGGGAAAGACCGTGTGTCTTGGCCAAAA
TTCGCAGTCCCCAACCTCCAATCACTCACCAACCTCCTGTCCTCCAACTTGTCCTG
GTTATCGCTGGATGTGTCTGCGGCGTTTTATCATCTTCCTCTTCATCCTGCTGCTAT
GCCTCATCTTCTTGTTGGTTCTTCTGGACTATCAAGGTATGTTGCCCGTGTGTCCTC
TAATTCCAGGATCCTCAACCACCAGCACGGGACCATGCCGAACCTGCACGACTCC
TGCTCAAGGAACCTCTATGTATCCCTCCTGTTGCTGTACCAAACCTTCGGACGGAA
ATTGCACCTGTATTCCCATCCCATCATCCTGGGCTTTCGGAAAATTCCTATGGGAG
TGGGCCTCAGCCCGTTTCTCATGGCTCAGTTTTCTAGTGCCATTTGTTCAGTGGTTC
GTAGGGCTTTCCCCCACTGTTTGGCTTTCAGTTATGTGGATGATGTGGTATTGGGG
GCCAAGTCTGTACAGCATCTTGAGTCCCTTTTACCGCTGTTACCAATTTTCTTTTG
TCTTTGGGTATACATTTAAATCCTAACAAAACAAAACGATGGGGTTACTCTCTGA
ATTTTATGGGTTATGTCATTGGATGTTATGGGTCCTTGCCACAAGAACACATCGTA
CAAAAAATCAAAGAATGT
(SEQ ID NO:6)

Figure 3

QAPVRKAAYPAVSTFEKHASSGHAVEHHNLPPNSARSQSERPVFPCWWLQFRNSKPC
SDYCLSLIVNLLEDWGPCTEHGEHHIRTPRTPSRVTGGVFLVDKNPHNTAESRLVVDF
SQFSRGKDRVSWPKFAVPNLQSLTNLLSSNLSWLSLDVSAAFYHLPLHPAAMPHLLV
GSSGLSRYVARVSSNSRILNHQHGTMPNLHDSCSRNLYVSLLLLYQTFGRKLHLYSHP
IILGFRKIPMGVGLSPFLMAQFSSAICSVVRRAFPHCLAFSYVDDVVLGAKSVQHLESL
FTAVTNFLLSLGIHLNPNKTKRWGYSLNFMGYVIGCYGSLPQEHIVQKIKEC
(SEQ ID NO:7)

Figure 4

Figure 5 Patient A HbsAg sequence sample A
KRQSGRQPTPLSPPLRNTHPQATQWNTTTFHQTLQDPRVKGLYFPAGGSSSGTVNPVP
TTASPLSSIFSRIGDPALNMENITSGLLGPLLVLQAGFFLLTKILTIPQSLDSWWTSLNFL
GGKTVCLGQNSQSPTSNHSPTSCPPTCPGYRWMCLRRFIIFLFILLLCLIFLLVLLDYQG
MLPVCPLIPGSSTTSTGPCRTCTTPAQGTSMYPSCCCTKPSDGNCTCIPIPSSWAFGKFL
WEWASARFSWLSFLVPFVQWFVGLSPTVWLSVMWMMWYWGPSLYSILSPFLPLLPI
FFCLWVYI*
(SEQ ID NO:8)

Figure 5

AAATCCGCCTCCTGCCTCCACCAAKCGCCAGTCAGGAAGGCAGCCTACCCCGCTG
TCTCCACCTTTGAGAAACACGCATCCTCAGGCCACGCAGTGGAACACCACAACCT
TCCACCAAACTCTGCAAGATCCCAGAGTGAAAGGCCTGTATTTCCTGCTGGTGG
CTCCAGTTCAGGAACAGTAAACCCTGTTCCGACTACTGCCTCTCCCTTATCGTCAA
TCTTCTCGAGGATTGGGGACCCTGCACTGAACATGGAGAACATCACATCAGGACT
CCTAGGACCCCTTCTCGTGTTACAGGCGGGGTTTTTCTTGTTGACAAAAATCCTCA
CAATACCGCAGAGTCTAGACTCGTGGTGGACTTCTCTCAATTTTCTAGGGGGAAM
TACCGTGTGTCTTGGCCAAAATTCGCAGTCCCCAACCTCCAATCACTCACCAACCT
CCTGTCCTCCAACTTGTCCTGGTTATCGCTGGATGTGTCTGCGGCGTTTTATCATCT
TCCTCTTCATCCTGCTGCTATGCCTCATCTTCTTGTTGGTTCTTCTGGACTATCAAG
GTATGTTGCCCGTGTGTCCTCTAATTCCAGGATCCTCAACCACCAGCACGGGACCA
TGCCGAACCTGCACGACTCCTGCTCAAGGAACCTCTATGTATCCCTCCTGTTGCTG
TACCAAACCTTCGGACGGAAATTGCACCTGTATTCCCATCCCATCATCCTGGGCTT
TCGGAAAATTCCTATGGGAGTGGGCCTCAGCCCGTTTCTCMTGGYTCAGTTTACT
AGTGCCATTTGTTCAGTGGTTCGTAGGGCTTTCCCCCACTGTTTGGCTTTCAGTTAT
ATGGATGATGTGGTATTGGGGGCCAAGTCTGTACAGCATCTTGAGTCCCTTTTTAC
CGCTGTTACCAATTTTCTTTTGTCTTTGGGTATACATTTAACCCCTAACAAAACAA
AACGATGGGGTTACTCTCTGAATTTTATGGGTTATG
(SEQ ID NO:9)

Figure 6

KSASCLHQ[A/S]PVRKAAYPAVSTFEKHASSGHAVEHHNLPPNSARSQSERPVFPCW
WLQFRNSKPCSDYCLSLIVNLLEDWGPCTEHGEHHIRTPRTPSRVTGGVFLVDKNPHN
TAESRLVVDFSQFSRG[K/N]YRVSWPKFAVPNLQSLTNLLSSNLSWLSLDVSAAFYHL
PLHPAAMPHLLVGSSGLSRYVARVSSNSRILNHQHGTMPNLHDSCSRNLYVSLLLLY
QTFGRKLHLYSHPIILGFRKIPMGVGLSPFL[M/L][A/V]QFTSAICSVVRRAFPHCLAFS
YMDDVVLGAKSVQHLESLFTAVTNFLLSLGIHLTPNKTKRWGYSLNFMGY
(SEQ ID NO:10)

Figure 7

NPPPAST[K/N]RQSGRQPTPLSPPLRNTHPQATQWNTTTFHQTLQDPRVKGLYFPAGG
SSSGTVNPVPTTASPLSSIFSRIGDPALNMENITSGLLGPLLVLQAGFFLLTKILTIPQSLD
SWWTSLNFLGG[N/T]TVCLGQNSQSPTSNHSPTSCPPTCPGYRWMCLRRFIIFLFILLLC
LIFLLVLLDYQGMLPVCPLIPGSSTTSTGPCRTCTTPAQGTSMYPSCCCTKPSDGNCTCI
PIPSSWAFGKFLWEWASARFSW[L/F]SLLVPFVQWFVGLSPTVWLSVIWMMWYWGP
SLYSILSPFLPLLPIFFCLWVYI*
(SEQ ID NO:11)

Figure 8

ATTTCCTCCTCCTGCCTCCACCAATCGGCAGTCAGGAAGGCAGCCTACTCCCATCT
CTCCACCTCTAAGAGACAGTCATCCTCAGGCCATGCAGTGGAATTCCACTGCCTTC
CACCAAGCTCTGCAGGATCCCAGAGTCAGGGGTCTGTATCTTCCTGCTGGTGGCTC
CAGTTCAGAAACAGTAAACCCTGCTCCGAATACTGCCTCTCACATATCGTCAATCT
CCGCGAGGACTGGGGACCCTGTGACGAACATGGAGAACATCACATCAGGACTCCT
AGGACCCTGCTCGTGTTACAGGCGGGGTTTTCTTGTTGACAAGAATCCTCACAA
TACCGCAGAGTCTAGACTCGTGGTGGACTTCTCTCAGTTTTCTAGGGGGGTCACCC
GTGTGTCTTGGCCAAAATTCGCAGTCCCCAACCTCCAATCACTCACCAACCTCCTG
TCCTCCAACTTGTCCTGGTTATCGCTGGATGTGTCTGCGGCATTTTATCATATTCCT
CTTCATCCTGCTGCTATGCCTCATCTTCTTATTGGTTCTTCTGGATTATCAAGGTAT
GTTGCCCGTTTGTCCTCTAATTCCAGGATCACCAACAACCAGTACGGGACCATGC
AAAACCTGCACGACTCCTGCTCAAGGCAACTCTATGTTTCCCTCCTGTTGCTGTAC
AAAACCTACGGATGGAAATTGCACCTGTATTCCCATCCCATCGTCCTGGGCTTTCG
CAAAATACCTATGGGAGTGGGCCTCAGTCCGTTTCTCATGGCTCAGTTTACTAGTG
CCATTTGTTCAGTGGTTCGTAGGGCTTTCCCCCACTGTTTGGCTTTCAGCTATGTGG
ATGATGTGGTATTGGGGGCCAAATCTGTACAGCACCGTGAGGCCCTTTATACCGC
TGTTACCAATTTTCTTTTGTCTCTGGGTATACATTTAAACCCTAACAAAACAAAAA
GATGGGGTTATTCCCTAAACTTCCTGGGTTACATAATTGGCAGTTGGGGAACATTA
CCACAGGATCATATTGTACAAAAGATCAAACACTG
(SEQ ID NO:12)

Figure 9

ISSSCLHQSAVRKAAYSHLSTSKRQSSSGHAVEFHCLPPSSAGSQSQGSVSSCWWLQF
RNSKPCSEYCLSHIVNLREDWGPCDEHGEHHIRTPRTPARVTGGVFLVDKNPHNTAES
RLVVDFSQFSRGVTRVSWPKFAVPNLQSLTNLLSSNLSWLSLDVSAAFYHIPLHPAAM
PHLLIGSSGLSRYVARLSSNSRITNNQYGTMQNLHDSCSRQLYVSLLLLYKTYGWKL
HLYSHPIVLGFRKIPMGVGLSPFLMAQFTSAICSVVRRAFPHCLAFSYVDDVVLGAKS
VQHREALYTAVTNFLLSLGIHLNPNKTKRWGYSLNFLGYIIGSWGTLPQDHIVQKIKH
(SEQ ID NO:13)

Figure 10

FPPPASTNRQSGRQPTPISPPLRDSHPQAMQWNSTAFHQALQDPRVRGLYLPAGGSSS
ETVNPAPNTASHISSISARTGDPVTNMENITSGLLGPLLVLQAGFFLLTRILTIPQSLDS
WWTSLSFLGGSPVCLGQNSQSPTSNHSPTSCPPTCPGYRWMCLRHFIIFLFILLLCLIFL
LVLLDYQGMLPVCPLIPGSPTTSTGPCKTCTTPAQGNSMFPSCCCTKPTDGNCTCIPIPS
SWAFAKYLWEWASVRFSWLSLLVPFVQWFVGLSPTVWLSAMWMMWYWGPNLYS
TVRPFIPLLPIFFCLWVYI
(SEQ ID NO:14)

Figure 11

ATTTCCTCCTCCTGCCTCCACCAATCGGCAGTCAGGAAGGCAGCCTACTCCCATCT
CTCCACCTCTAAGAGACAGTCATCCTCAGGCCATGCAGTGGAATTCCACTGCCTTC
CACCAAGCTCTGCAGGATCCCAGAGTCAGGGGTCTGTATCTTCCTGCTGGTGGCTC
CAGTTCAGAAACAGTAAACCCTGCTCCGAATACTGCCTCTCACATATCGTCAATCT
CCGCGAGGACTGGGGACCCTGTGACGAACATGGAGAACATCACATCAGGACTCCT
AGGACCCCTGCTCGTGTTACAGGCGGGGTTTTTCTTGTTGACAAGAATCCTCACAA
TACCGCAGAGTCTAGACTCGTGGTGGACTTCTCTCAGTTTTCTAGGGGGGTCACCC
GTGTGTCTTGGCCAAAATTCGCAGTCCCCAACCTCCAATCACTCACCAACCTCCTG
TCCTCCAACTTGTCCTGGTTATCGCTGGATGTGTCTGCGGCATTTTATCATATTCCT
CTTCATCCTGCTGCTATGCCTCATCTTCTTATTGGTTCTTCTGGATTATCAAGGTAT
GTTGCCCGTTTGTCCTCTAATTCCAGGATCACCAACAACCAGTACGGGACCATGC
AAAACCTGCACGACTCCTGCTCAAGGCAACTCTATGTTTCCCTCCTGTTGCTGTAC
AAAACCTACGGATGGAAATTGCACCTGTATTCCCATCCCATCGTCCTGGGCTTTCG
CAAAATACCTATGGGAGTGGGCCTCAGTCCGTTTCTCATGGCTCAGTTTACTAGTG
CCATTTGTTCAGTGGTTCGTAGGGCTTTCCCCCACTGTTTGGCTTTCAGCTATGTGG
ATGATGTGGTATTGGGGGCCAAATCTGTACAGCACCGTGAGGCCCTTTATACCGC
TGTTACCAATTTTCTTTTGTCTCTGGGTATACATTTAAACCCTAACAAAACAAAAA
GATGGGGTTATTCCCTAAACTTCCTGGGTTACATAATTGGCAGTTGGGGAACATTA
CCACAGGATCATATTGTACAAAAGATCAAACACTG
(SEQ ID NO:15)

Figure 12

ISSSCLHQSAVRKAAYSHLSTSKRQSSSGHAVEFHCLPPSSAGSQSQGSVSSCWWLQF
RNSKPCSEYCLSHIVNLREDWGPCDEHGEHHIRTPRTPARVTGGVFLVDKNPHNTAES
RLVVDFSQFSRGVTRVSWPKFAVPNLQSLTNLLSSNLSWLSLDVSAAFYHIPLHPAAM
PHLLIGSSGLSRYVARLSSNSRITNNQYGTMQNLHDSCSRQLYVSLLLLYKTYGWKL
HLYSHPIVLGFRKIPMGVGLSPFLMAQFTSAICSVVRRAFPHCLAFSYVDDVVLGAKS
VQHREALYTAVTNFLLSLGIHLNPNKTKRWGYSLNFLGYIIGSWGTLPQDHIVQKIKH
(SEQ ID NO:16)

Figure 13

FPPPASTNRQSGRQPTPISPPLRDSHPQAMQWNSTAFHQALQDPRVRGLYLPAGGSSS
ETVNPAPNTASHISSISARTGDPVTNMENITSGLLGPLLVLQAGFFLLTRILTIPQSLDS
WWTSLSFLGGSPVCLGQNSQSPTSNHSPTSCPPTCPGYRWMCLRHFIIFLFILLLCLIFL
LVLLDYQGMLPVCPLIPGSPTTSTGPCKTCTTPAQGNSMFPSCCCTKPTDGNCTCIPIPS
SWAFAKYLWEWASVRFSWLSLLVPFVQWFVGLSPTVWLSAMWMMWYWGPNLYS
TVRPFIPLLPIFFCLWVYI
(SEQ ID NO:17)

Figure 14

AATCCGCCTCCTGCCTCTACCAATCGCCAGTCAGGAAGGCAGCCTACCCCTCYGA
CTCCACCTTTGAGAAACACTCATCCTCAGGCCATGYAGTGGAACTCCACAAACTT
CCACCGAACTCTACAAGATCCCAGAGTGAAAGGCCTGTATCTCCCTGCTGGTGGC
TCCAGTTCAGGAACAGTAAACCCTGTTCCGACTACTGTCTCTCACACATCGTCAAT
CTTATCGAGGATTGGGGACCCTGCACTGAACATGGAGAACATCACATCAGGATTC
CTAGGACCCCTGCTCGCGTTACAGGCGGGGTTTTCTCGTTGACAAGAATCCTCAC
AATACCGCAGAGTCTAGACTCGTGGTGGACTTCTCTCAATTTTCTAGGGGAGACC
ACCGTGTGCCTTGGCCAAAATTCGCAGTCCCCAACCTCCAATCACTCACCAACCTC
CTGTCCTCCAACTTGTCCTGGTTATCGCTGGATGTGTCTGCGGCGTTTATCATATT
CCTCTTCATCCTGCTGCTATGCCTCATCTTCTTGTTGGTTCTTCTGGACTATCAAGG
TATGTTGCCCGTTTGCCCTCTAATTCCAGGATCCTCAACCACCAGCACGGGACCAT
GCAGAACCTGCACGTCTCCTGCTCAAAGGAACTCTACGTATCCCTCCTGTTGCTGT
ACAAAACCTTCGGACGGAAATTGCACCTGTATTCCCATCCCATCATCCTGGGCTTT
CGGAAAATTCCTATGGGAGTGGGCCTCAGCCCGTTTCTCCTTACTCAGTTTACTAG
TGCCATTTGTTCAGTGGTTCGTAGGGCTTTCCCCCACTGTTTGGCTTTCAGTTATAT
GGATGATGTGGTATTGGGGGCCAGGTCTGTACAGCATCGTGAGGCCCTTTTTACC
GCTGTTACCAATTTTCTTTTGTCTCTGGGTGTACATTTAACCCCGAACAAAACAAA
AAGATGGGGTTACTCTTTACATTTCCTGGGCTATGTCATTGGATGTTATGGGTCAT
TGCCACAAGAT (SEQ ID NO:18)

Figure 15

SASCLYQSPVRKAAYPSDSTFEKHSSSGHXVELHKLPPNSTRSQSERPVSPCWWLQFR
NSKPCSDYCLSHIVNLIEDWGPCTEHGEHHIRIPRTPARVTGGVFLVDKNPHNTAESRL
VVDFSQFSRGDHRVPWPKFAVPNLQSLTNLLSSNLSWLSLDVSAAFYHIPLHPAAMP
HLLVGSSGLSRYVARLPSNSRILNHQHGTMQNLHVSCSKELYVSLLLLYKTFGRKLHL
YSHPIILGFRKIPMGVGLSPFLLTQFTSAICSVVRRAFPHCLAFSYMDDVVLGARSVQH
REALFTAVTNFLLSLGVHLTPNKTKRWGYSLHFLGYVIGCYGSLPQD
(SEQ ID NO:19)

Figure 16

NPPPASTNRQSGRQPTPXTPPLRNTHPQAMXWNSTNFHRTLQDPRVKGLYLPAGGSS
SGTVNPVPTTVSHTSSILSRIGDPALNMENITSGFLGPLLALQAGFFSLTRILTIPQSLDS
WWTSLNFLGETTVCLGQNSQSPTSNHSPTSCPPTCPGYRWMCLRRFIIFLFILLLCLIFL
LVLLDYQGMLPVCPLIPGSSTTSTGPCRTCTSPAQRNSTYPSCCCTKPSDGNCTCIPIPS
SWAFGKFLWEWASARFSLLSLLVPFVQWFVGLSPTVWLSVIWMMWYWGPGLYSIV
RPFLPLLPIFFCLWVYI
(SEQ ID NO:20)

Figure 17

SEQUENCE LISTING

```
<160> NUMBER OF SEQ ID NOS: 20

<210> SEQ ID NO 1
<211> LENGTH: 23
<212> TYPE: DNA
<213> ORGANISM: Hep B virus

<400> SEQUENCE: 1
gcctcatttt gtgggtcacc ata                                              23

<210> SEQ ID NO 2
<211> LENGTH: 18
<212> TYPE: DNA
<213> ORGANISM: Hep B virus

<400> SEQUENCE: 2
aaattcgcag tccccaaa                                                    18

<210> SEQ ID NO 3
<211> LENGTH: 21
<212> TYPE: DNA
<213> ORGANISM: Hep B virus

<400> SEQUENCE: 3
ttggggtgga gccctcaggc t                                                21

<210> SEQ ID NO 4
<211> LENGTH: 18
<212> TYPE: DNA
<213> ORGANISM: Hep B virus

<400> SEQUENCE: 4
```

-continued

```
gaaaattggt aacagcgg                                                    18

<210> SEQ ID NO 5
<211> LENGTH: 20
<212> TYPE: DNA
<213> ORGANISM: Hep B virus

<400> SEQUENCE: 5
tctctgacat actttccaat                                                  20

<210> SEQ ID NO 6
<211> LENGTH: 1023
<212> TYPE: DNA
<213> ORGANISM: Hep B virus

<400> SEQUENCE: 6
caagcgccag tcaggaaggc agcctacccc gctgtctcca cctttgagaa acacgcatcc      60
tcaggccacg cagtggaaca ccacaacctt ccaccaaact ctgcaagatc ccagagtgaa     120
aggcctgtat ttccctgctg gtggctccag ttcaggaaca gtaaaccctg ttccgactac    180
tgcctctccc ttatcgtcaa tcttctcgag gattggggac cctgcactga acatggagaa    240
catcacatca ggactcctag gacccctttct cgtgttacag gcggggtttt tcttgttgac    300
aaaaatcctc acaataccgc agagtctaga ctcgtggtgg acttctctca attttctagg    360
gggaaagacc gtgtgtcttg gccaaaattc gcagtcccca acctccaatc actcaccaac    420
ctcctgtcct ccaacttgtc ctggttatcg ctggatgtgt ctgcggcgtt ttatcatctt    480
cctcttcatc ctgctgctat gcctcatctt cttgttggtt cttctggact atcaaggtat    540
gttgcccgtg tgtcctctaa ttccaggatc tcaaccacc agcacgggac catgccgaac     600
ctgcacgact cctgctcaag gaacctctat gtatccctcc tgttgctgta ccaaaccttc    660
ggacggaaat tgcacctgta ttcccatccc atcatcctgg ctttcggaa aattcctatg     720 ggagtgggcc tcagcccgtt tctcatggct cagttttcta gtgccatttg ttcagtggtt    780
cgtagggctt tcccccactg tttggctttc agttatgtgg atgatgtggt attgggggcc    840
aagtctgtac agcatcttga gtcccttttt accgctgtta ccaattttct tttgtctttg    900
ggtatacatt taaatcctaa caaaacaaaa cgatgggggtt actctctgaa ttttatgggt    960
tatgtcattg gatgttatgg gtccttgcca caagaacaca tcgtacaaaa aatcaaagaa   1020
tgt                                                                 1023

<210> SEQ ID NO 7
<211> LENGTH: 341
<212> TYPE: PRT
<213> ORGANISM: Hep B virus

<400> SEQUENCE: 7

Gln Ala Pro Val Arg Lys Ala Ala Tyr Pro Ala Val Ser Thr Phe Glu
1               5                   10                  15

Lys His Ala Ser Ser Gly His Ala Val Glu His His Asn Leu Pro Pro
            20                  25                  30

Asn Ser Ala Arg Ser Gln Ser Glu Arg Pro Val Phe Pro Cys Trp Trp
        35                  40                  45

Leu Gln Phe Arg Asn Ser Lys Pro Cys Ser Asp Tyr Cys Leu Ser Leu
    50                  55                  60

Ile Val Asn Leu Leu Glu Asp Trp Gly Pro Cys Thr Glu His Gly Glu
65                  70                  75                  80
```

```
His His Ile Arg Thr Pro Arg Thr Pro Ser Arg Val Thr Gly Gly Val
                85                  90                  95

Phe Leu Val Asp Lys Asn Pro His Asn Thr Ala Glu Ser Arg Leu Val
            100                 105                 110

Val Asp Phe Ser Gln Phe Ser Arg Gly Lys Asp Arg Val Ser Trp Pro
        115                 120                 125

Lys Phe Ala Val Pro Asn Leu Gln Ser Leu Thr Asn Leu Leu Ser Ser
130                 135                 140

Asn Leu Ser Trp Leu Ser Leu Asp Val Ser Ala Ala Phe Tyr His Leu
145                 150                 155                 160

Pro Leu His Pro Ala Ala Met Pro His Leu Leu Val Gly Ser Ser Gly
                165                 170                 175

Leu Ser Arg Tyr Val Ala Arg Val Ser Ser Asn Ser Arg Ile Leu Asn
            180                 185                 190

His Gln His Gly Thr Met Pro Asn Leu His Asp Ser Cys Ser Arg Asn
        195                 200                 205

Leu Tyr Val Ser Leu Leu Leu Leu Tyr Gln Thr Phe Gly Arg Lys Leu
    210                 215                 220

His Leu Tyr Ser His Pro Ile Ile Leu Gly Phe Arg Lys Ile Pro Met
225                 230                 235                 240

Gly Val Gly Leu Ser Pro Phe Leu Met Ala Gln Phe Ser Ser Ala Ile
                245                 250                 255

Cys Ser Val Val Arg Arg Ala Phe Pro His Cys Leu Ala Phe Ser Tyr
            260                 265                 270

Val Asp Asp Val Val Leu Gly Ala Lys Ser Val Gln His Leu Glu Ser
        275                 280                 285

Leu Phe Thr Ala Val Thr Asn Phe Leu Leu Ser Leu Gly Ile His Leu
    290                 295                 300

Asn Pro Asn Lys Thr Lys Arg Trp Gly Tyr Ser Leu Asn Phe Met Gly
305                 310                 315                 320

Tyr Val Ile Gly Cys Tyr Gly Ser Leu Pro Gln Glu His Ile Val Gln
                325                 330                 335

Lys Ile Lys Glu Cys
            340

<210> SEQ ID NO 8
<211> LENGTH: 303
<212> TYPE: PRT
<213> ORGANISM: Hep B virus

<400> SEQUENCE: 8

Lys Arg Gln Ser Gly Arg Gln Pro Thr Pro Leu Ser Pro Pro Leu Arg
1               5                   10                  15

Asn Thr His Pro Gln Ala Thr Gln Trp Asn Thr Thr Thr Phe His Gln
            20                  25                  30

Thr Leu Gln Asp Pro Arg Val Lys Gly Leu Tyr Phe Pro Ala Gly Gly
        35                  40                  45

Ser Ser Ser Gly Thr Val Asn Pro Val Pro Thr Thr Ala Ser Pro Leu
    50                  55                  60

Ser Ser Ile Phe Ser Arg Ile Gly Asp Pro Ala Leu Asn Met Glu Asn
65                  70                  75                  80

Ile Thr Ser Gly Leu Leu Gly Pro Leu Leu Val Leu Gln Ala Gly Phe
                85                  90                  95

Phe Leu Leu Thr Lys Ile Leu Thr Ile Pro Gln Ser Leu Asp Ser Trp
```

-continued

|  | 100 |  |  |  | 105 |  |  |  | 110 |  |  |
|---|---|---|---|---|---|---|---|---|---|---|---|
| Trp | Thr | Ser | Leu | Asn | Phe | Leu | Gly | Gly | Lys | Thr | Val | Cys | Leu | Gly | Gln |
|  |  | 115 |  |  |  | 120 |  |  |  | 125 |  |

Asn Ser Gln Ser Pro Thr Ser Asn His Ser Pro Thr Ser Cys Pro Pro
    130                 135                 140

Thr Cys Pro Gly Tyr Arg Trp Met Cys Leu Arg Arg Phe Ile Ile Phe
145                 150                 155                 160

Leu Phe Ile Leu Leu Leu Cys Leu Ile Phe Leu Leu Val Leu Leu Asp
                165                 170                 175

Tyr Gln Gly Met Leu Pro Val Cys Pro Leu Ile Pro Gly Ser Ser Thr
            180                 185                 190

Thr Ser Thr Gly Pro Cys Arg Thr Cys Thr Thr Pro Ala Gln Gly Thr
        195                 200                 205

Ser Met Tyr Pro Ser Cys Cys Cys Thr Lys Pro Ser Asp Gly Asn Cys
    210                 215                 220

Thr Cys Ile Pro Ile Pro Ser Ser Trp Ala Phe Gly Lys Phe Leu Trp
225                 230                 235                 240

Glu Trp Ala Ser Ala Arg Phe Ser Trp Leu Ser Phe Leu Val Pro Phe
                245                 250                 255

Val Gln Trp Phe Val Gly Leu Ser Pro Thr Val Trp Leu Ser Val Met
            260                 265                 270

Trp Met Met Trp Tyr Trp Gly Pro Ser Leu Tyr Ser Ile Leu Ser Pro
        275                 280                 285

Phe Leu Pro Leu Leu Pro Ile Phe Phe Cys Leu Trp Val Tyr Ile
    290                 295                 300

<210> SEQ ID NO 9
<211> LENGTH: 985
<212> TYPE: DNA
<213> ORGANISM: Hep B virus

<400> SEQUENCE: 9
aaatccgcct cctgcctcca ccaakcgcca gtcaggaagg cagcctaccc cgctgtctcc      60
acctttgaga aacacgcatc ctcaggccac gcagtggaac accacaacct tccaccaaac     120
tctgcaagat cccagagtga aaggcctgta tttccctgct ggtggctcca gttcaggaac     180
agtaaaccct gttccgacta ctgcctctcc cttatcgtca atcttctcga ggattgggga     240
ccctgcactg aacatggaga acatcacatc aggactccta ggaccccttc tcgtgttaca     300
ggcggggttt ttcttgttga caaaaatcct cacaataccg cagagtctag actcgtggtg     360
gacttctctc aattttctag ggggaamtac cgtgtgtctt ggccaaaatt cgcagtcccc     420
aacctccaat cactcaccaa cctcctgtcc tccaacttgt cctggttatc gctggatgtg     480
tctgcggcgt tttatcatct tcctcttcat cctgctgcta tgcctcatct tcttgttggt     540
tcttctggac tatcaaggta tgttgcccgt gtgtcctcta attccaggat cctcaaccac     600
cagcacggga ccatgccgaa cctgcacgac tcctgctcaa ggaacctcta tgtatccctc     660
ctgttgctgt accaaacctt cggacggaaa ttgcacctgt attcccatcc catcatcctg     720
ggctttcgga aaattcctat gggagtgggc ctcagcccgt ttctcmtggy tcagtttact     780
agtgccattt gttcagtggt tcgtagggct ttcccccact gtttggcttt cagttatatg     840
gatgatgtgg tattgggggc caagtctgta cagcatcttg agtcccttttt accgctgtt     900
accaattttc ttttgtcttt gggtatacat ttaaccccta caaaacaaa cgatggggt      960
tactctctga attttatggg ttatg                                          985

<210> SEQ ID NO 10
<211> LENGTH: 332
<212> TYPE: PRT
<213> ORGANISM: Hep B virus

<400> SEQUENCE: 10

```
Lys Ser Ala Ser Cys Leu His Gln Ala Ser Pro Val Arg Lys Ala Ala
1               5                   10                  15

Tyr Pro Ala Val Ser Thr Phe Glu Lys His Ala Ser Ser Gly His Ala
            20                  25                  30

Val Glu His His Asn Leu Pro Pro Asn Ser Ala Arg Ser Gln Ser Glu
        35                  40                  45

Arg Pro Val Phe Pro Cys Trp Trp Leu Gln Phe Arg Asn Ser Lys Pro
    50                  55                  60

Cys Ser Asp Tyr Cys Leu Ser Leu Ile Val Asn Leu Leu Glu Asp Trp
65                  70                  75                  80

Gly Pro Cys Thr Glu His Gly Glu His His Ile Arg Thr Pro Arg Thr
                85                  90                  95

Pro Ser Arg Val Thr Gly Gly Val Phe Leu Val Asp Lys Asn Pro His
            100                 105                 110

Asn Thr Ala Glu Ser Arg Leu Val Val Asp Phe Ser Gln Phe Ser Arg
        115                 120                 125

Gly Lys Asn Tyr Arg Val Ser Trp Pro Lys Phe Ala Val Pro Asn Leu
    130                 135                 140

Gln Ser Leu Thr Asn Leu Leu Ser Ser Asn Leu Ser Trp Leu Ser Leu
145                 150                 155                 160

Asp Val Ser Ala Ala Phe Tyr His Leu Pro Leu His Pro Ala Ala Met
                165                 170                 175

Pro His Leu Leu Val Gly Ser Ser Gly Leu Ser Arg Tyr Val Ala Arg
            180                 185                 190

Val Ser Ser Asn Ser Arg Ile Leu Asn His Gln His Gly Thr Met Pro
        195                 200                 205

Asn Leu His Asp Ser Cys Ser Arg Asn Leu Tyr Val Ser Leu Leu Leu
    210                 215                 220

Leu Tyr Gln Thr Phe Gly Arg Lys Leu His Leu Tyr Ser His Pro Ile
225                 230                 235                 240

Ile Leu Gly Phe Arg Lys Ile Pro Met Gly Val Gly Leu Ser Pro Phe
                245                 250                 255

Leu Met Leu Ala Val Gln Phe Thr Ser Ala Ile Cys Ser Val Val Arg
            260                 265                 270

Arg Ala Phe Pro His Cys Leu Ala Phe Ser Tyr Met Asp Asp Val Val
        275                 280                 285

Leu Gly Ala Lys Ser Val Gln His Leu Glu Ser Leu Phe Thr Ala Val
    290                 295                 300

Thr Asn Phe Leu Leu Ser Leu Gly Ile His Leu Thr Pro Asn Lys Thr
305                 310                 315                 320

Lys Arg Trp Gly Tyr Ser Leu Asn Phe Met Gly Tyr
                325                 330
```

<210> SEQ ID NO 11
<211> LENGTH: 313
<212> TYPE: PRT
<213> ORGANISM: Hep B virus

<400> SEQUENCE: 11

Asn Pro Pro Pro Ala Ser Thr Lys Asn Arg Gln Ser Gly Arg Gln Pro
1               5                   10                  15

Thr Pro Leu Ser Pro Pro Leu Arg Asn Thr His Pro Gln Ala Thr Gln
            20                  25                  30

Trp Asn Thr Thr Thr Phe His Gln Thr Leu Gln Asp Pro Arg Val Lys
                35                  40                  45

Gly Leu Tyr Phe Pro Ala Gly Gly Ser Ser Ser Gly Thr Val Asn Pro
    50                  55                  60

Val Pro Thr Thr Ala Ser Pro Leu Ser Ser Ile Phe Ser Arg Ile Gly
65                  70                  75                  80

Asp Pro Ala Leu Asn Met Glu Asn Ile Thr Ser Gly Leu Leu Gly Pro
                85                  90                  95

Leu Leu Val Leu Gln Ala Gly Phe Phe Leu Leu Thr Lys Ile Leu Thr
            100                 105                 110

Ile Pro Gln Ser Leu Asp Ser Trp Trp Thr Ser Leu Asn Phe Leu Gly
            115                 120                 125

Gly Asn Thr Thr Val Cys Leu Gly Gln Asn Ser Gln Ser Pro Thr Ser
130                 135                 140

Asn His Ser Pro Thr Ser Cys Pro Pro Thr Cys Pro Gly Tyr Arg Trp
145                 150                 155                 160

Met Cys Leu Arg Arg Phe Ile Ile Phe Leu Phe Ile Leu Leu Leu Cys
            165                 170                 175

Leu Ile Phe Leu Leu Val Leu Leu Asp Tyr Gln Gly Met Leu Pro Val
            180                 185                 190

Cys Pro Leu Ile Pro Gly Ser Ser Thr Thr Ser Thr Gly Pro Cys Arg
            195                 200                 205

Thr Cys Thr Thr Pro Ala Gln Gly Thr Ser Met Tyr Pro Ser Cys Cys
    210                 215                 220

Cys Thr Lys Pro Ser Asp Gly Asn Cys Thr Cys Ile Pro Ile Pro Ser
225                 230                 235                 240

Ser Trp Ala Phe Gly Lys Phe Leu Trp Glu Trp Ala Ser Ala Arg Phe
                245                 250                 255

Ser Trp Leu Phe Ser Leu Leu Val Pro Phe Val Gln Trp Phe Val Gly
            260                 265                 270

Leu Ser Pro Thr Val Trp Leu Ser Val Ile Trp Met Met Trp Tyr Trp
            275                 280                 285

Gly Pro Ser Leu Tyr Ser Ile Leu Ser Pro Phe Leu Pro Leu Leu Pro
    290                 295                 300

Ile Phe Phe Cys Leu Trp Val Tyr Ile
305                 310

<210> SEQ ID NO 12
<211> LENGTH: 1043
<212> TYPE: DNA
<213> ORGANISM: Hep B virus

<400> SEQUENCE: 12
atttcctcct cctgcctcca ccaatcggca gtcaggaagg cagcctactc ccatctctcc      60
acctctaaga gacagtcatc ctcaggccat gcagtggaat tccactgcct tccaccaagc     120
tctgcaggat cccagagtca ggggtctgta tcttcctgct ggtggctcca gttcagaaac     180
agtaaaccct gctccgaata ctgcctctca catatcgtca atctccgcga ggactgggga     240
ccctgtgacg aacatggaga acatcacatc aggactccta ggaccctgc tcgtgttaca      300

```
ggcggggttt tcttgttga caagaatcct cacaataccg cagagtctag actcgtggtg    360
gacttctctc agttttctag gggggtcacc cgtgtgtctt ggccaaaatt cgcagtcccc    420
aacctccaat cactcaccaa cctcctgtcc tccaacttgt cctggttatc gctggatgtg    480
tctgcggcat tttatcatat tcctcttcat cctgctgcta tgcctcatct tcttattggt    540
tcttctggat tatcaaggta tgttgcccgt ttgtcctcta attccaggat caccaacaac    600
cagtacggga ccatgcaaaa cctgcacgac tcctgctcaa ggcaactcta tgtttccctc    660
ctgttgctgt acaaaaccta cggatggaaa ttgcacctgt attcccatcc catcgtcctg    720
ggctttcgca aaataccat gggagtgggc ctcagtccgt ttctcatggc tcagtttact    780
agtgccattt gttcagtggt tcgtagggct ttcccccact gtttggcttt cagctatgtg    840
gatgatgtgg tattggggc caaatctgta cagcaccgtg aggccctta taccgctgtt    900 accaattttc ttttgtctct gggtatacat ttaaaccta caaaacaaa aagatggggt    960 tattccctaa acttcctggg ttacataatt ggcagttggg gaacattacc acaggatcat   1020
attgtacaaa agatcaaaca ctg                                           1043
```

<210> SEQ ID NO 13
<211> LENGTH: 347
<212> TYPE: PRT
<213> ORGANISM: Hep B virus

<400> SEQUENCE: 13

```
Ile Ser Ser Ser Cys Leu His Gln Ser Ala Val Arg Lys Ala Ala Tyr
1               5                   10                  15

Ser His Leu Ser Thr Ser Lys Arg Gln Ser Ser Ser Gly His Ala Val
            20                  25                  30

Glu Phe His Cys Leu Pro Pro Ser Ala Gly Ser Gln Ser Gln Gly
        35                  40                  45

Ser Val Ser Ser Cys Trp Trp Leu Gln Phe Arg Asn Ser Lys Pro Cys
    50                  55                  60

Ser Glu Tyr Cys Leu Ser His Ile Val Asn Leu Arg Glu Asp Trp Gly
65                  70                  75                  80

Pro Cys Asp Glu His Gly Glu His His Ile Arg Thr Pro Arg Thr Pro
                85                  90                  95

Ala Arg Val Thr Gly Gly Val Phe Leu Val Asp Lys Asn Pro His Asn
            100                 105                 110

Thr Ala Glu Ser Arg Leu Val Val Asp Phe Ser Gln Phe Ser Arg Gly
        115                 120                 125

Val Thr Arg Val Ser Trp Pro Lys Phe Ala Val Pro Asn Leu Gln Ser
    130                 135                 140

Leu Thr Asn Leu Leu Ser Ser Asn Leu Ser Trp Leu Ser Leu Asp Val
145                 150                 155                 160

Ser Ala Ala Phe Tyr His Ile Pro Leu His Pro Ala Ala Met Pro His
                165                 170                 175

Leu Leu Ile Gly Ser Ser Gly Leu Ser Arg Tyr Val Ala Arg Leu Ser
            180                 185                 190

Ser Asn Ser Arg Ile Thr Asn Asn Gln Tyr Gly Thr Met Gln Asn Leu
        195                 200                 205

His Asp Ser Cys Ser Arg Gln Leu Tyr Val Ser Leu Leu Leu Leu Tyr
    210                 215                 220

Lys Thr Tyr Gly Trp Lys Leu His Leu Tyr Ser His Pro Ile Val Leu
225                 230                 235                 240
```

```
Gly Phe Arg Lys Ile Pro Met Gly Val Gly Leu Ser Pro Phe Leu Met
                245                 250                 255

Ala Gln Phe Thr Ser Ala Ile Cys Ser Val Val Arg Arg Ala Phe Pro
            260                 265                 270

His Cys Leu Ala Phe Ser Tyr Val Asp Asp Val Leu Gly Ala Lys
        275                 280                 285

Ser Val Gln His Arg Glu Ala Leu Tyr Thr Ala Val Thr Asn Phe Leu
    290                 295                 300

Leu Ser Leu Gly Ile His Leu Asn Pro Asn Lys Thr Lys Arg Trp Gly
305                 310                 315                 320

Tyr Ser Leu Asn Phe Leu Gly Tyr Ile Ile Gly Ser Trp Gly Thr Leu
                325                 330                 335

Pro Gln Asp His Ile Val Gln Lys Ile Lys His
            340                 345

<210> SEQ ID NO 14
<211> LENGTH: 310
<212> TYPE: PRT
<213> ORGANISM: Hep B virus

<400> SEQUENCE: 14

Phe Pro Pro Pro Ala Ser Thr Asn Arg Gln Ser Gly Arg Gln Pro Thr
1               5                   10                  15

Pro Ile Ser Pro Pro Leu Arg Asp Ser His Pro Gln Ala Met Gln Trp
            20                  25                  30

Asn Ser Thr Ala Phe His Gln Ala Leu Gln Asp Pro Arg Val Arg Gly
        35                  40                  45

Leu Tyr Leu Pro Ala Gly Gly Ser Ser Glu Thr Val Asn Pro Ala
    50                  55                  60

Pro Asn Thr Ala Ser His Ile Ser Ser Ile Ser Ala Arg Thr Gly Asp
65                  70                  75                  80

Pro Val Thr Asn Met Glu Asn Ile Thr Ser Gly Leu Leu Gly Pro Leu
                85                  90                  95

Leu Val Leu Gln Ala Gly Phe Phe Leu Leu Thr Arg Ile Leu Thr Ile
            100                 105                 110

Pro Gln Ser Leu Asp Ser Trp Trp Thr Ser Leu Ser Phe Leu Gly Gly
        115                 120                 125

Ser Pro Val Cys Leu Gly Gln Asn Ser Gln Ser Pro Thr Ser Asn His
130                 135                 140

Ser Pro Thr Ser Cys Pro Pro Thr Cys Pro Gly Tyr Arg Trp Met Cys
145                 150                 155                 160

Leu Arg His Phe Ile Ile Phe Leu Phe Ile Leu Leu Leu Cys Leu Ile
                165                 170                 175

Phe Leu Leu Val Leu Leu Asp Tyr Gln Gly Met Leu Pro Val Cys Pro
            180                 185                 190

Leu Ile Pro Gly Ser Pro Thr Thr Ser Thr Gly Pro Cys Lys Thr Cys
        195                 200                 205

Thr Thr Pro Ala Gln Gly Asn Ser Met Phe Pro Ser Cys Cys Cys Thr
    210                 215                 220

Lys Pro Thr Asp Gly Asn Cys Thr Cys Ile Pro Ile Pro Ser Ser Trp
225                 230                 235                 240

Ala Phe Ala Lys Tyr Leu Trp Glu Trp Ala Ser Val Arg Phe Ser Trp
                245                 250                 255

Leu Ser Leu Leu Val Pro Phe Val Gln Trp Phe Val Gly Leu Ser Pro
            260                 265                 270
```

```
Thr Val Trp Leu Ser Ala Met Trp Met Met Trp Tyr Trp Gly Pro Asn
        275                 280                 285

Leu Tyr Ser Thr Val Arg Pro Phe Ile Pro Leu Leu Pro Ile Phe Phe
        290                 295                 300

Cys Leu Trp Val Tyr Ile
305                 310

<210> SEQ ID NO 15
<211> LENGTH: 1043
<212> TYPE: DNA
<213> ORGANISM: Hep B virus

<400> SEQUENCE: 15
atttcctcct cctgcctcca ccaatcggca gtcaggaagg cagcctactc ccatctctcc      60
acctctaaga gacagtcatc ctcaggccat gcagtggaat tccactgcct tccaccaagc     120
tctgcaggat cccagagtca ggggtctgta tcttcctgct ggtggctcca gttcagaaac     180
agtaaaccct gctccgaata ctgcctctca catatcgtca atctccgcga ggactgggga     240
ccctgtgacg aacatggaga acatcacatc aggactccta ggaccctgc tcgtgttaca      300
ggcggggttt ttcttgttga caagaatcct cacaataccg cagagtctag actcgtggtg     360
gacttctctc agttttctag ggggtcacc cgtgtgtctt ggccaaaatt cgcagtcccc      420
aacctccaat cactcaccaa cctcctgtcc tccaacttgt cctggttatc gctggatgtg     480
tctgcggcat tttatcatat tcctcttcat cctgctgcta tgcctcatct tcttattggt     540
tcttctggat tatcaaggta tgttgcccgt ttgtcctcta attccaggat caccaacaac     600
cagtacggga ccatgcaaaa cctgcacgac tcctgctcaa ggcaactcta tgtttccctc     660
ctgttgctgt acaaaaccta cggatggaaa ttgcacctgt attcccatcc catcgtcctg     720
ggctttcgca aaataccat gggagtgggc ctcagtccgt ttctcatggc tcagtttact      780
agtgccattt gttcagtggt tcgtagggct ttccccccact gtttggcttt cagctatgtg     840
gatgatgtgg tattgggggc caaatctgta cagcaccgtg aggcccttta taccgctgtt     900
accaattttc ttttgtctct gggtatacat ttaaaccct acaaaacaaa agatggggt      960
tattccctaa acttcctggg ttacataatt ggcagttggg gaacattacc acaggatcat    1020
attgtacaaa agatcaaaca ctg                                             1043

<210> SEQ ID NO 16
<211> LENGTH: 347
<212> TYPE: PRT
<213> ORGANISM: Hep B virus

<400> SEQUENCE: 16

Ile Ser Ser Ser Cys Leu His Gln Ser Ala Val Arg Lys Ala Ala Tyr
1               5                   10                  15

Ser His Leu Ser Thr Ser Lys Arg Gln Ser Ser Gly His Ala Val
            20                  25                  30

Glu Phe His Cys Leu Pro Pro Ser Ser Ala Gly Ser Gln Ser Gln Gly
            35                  40                  45

Ser Val Ser Ser Cys Trp Trp Leu Gln Phe Arg Asn Ser Lys Pro Cys
    50                  55                  60

Ser Glu Tyr Cys Leu Ser His Ile Val Asn Leu Arg Glu Asp Trp Gly
65              70                  75                  80

Pro Cys Asp Glu His Gly Glu His His Ile Arg Thr Pro Arg Thr Pro
                85                  90                  95
```

Ala Arg Val Thr Gly Gly Val Phe Leu Val Asp Lys Asn Pro His Asn
            100                 105                 110

Thr Ala Glu Ser Arg Leu Val Val Asp Phe Ser Gln Phe Ser Arg Gly
            115                 120                 125

Val Thr Arg Val Ser Trp Pro Lys Phe Ala Val Pro Asn Leu Gln Ser
130                 135                 140

Leu Thr Asn Leu Leu Ser Ser Asn Leu Ser Trp Leu Ser Leu Asp Val
145                 150                 155                 160

Ser Ala Ala Phe Tyr His Ile Pro Leu His Pro Ala Ala Met Pro His
                165                 170                 175

Leu Leu Ile Gly Ser Ser Gly Leu Ser Arg Tyr Val Ala Arg Leu Ser
            180                 185                 190

Ser Asn Ser Arg Ile Thr Asn Gln Tyr Gly Thr Met Gln Asn Leu
            195                 200                 205

His Asp Ser Cys Ser Arg Gln Leu Tyr Val Ser Leu Leu Leu Leu Tyr
        210                 215                 220

Lys Thr Tyr Gly Trp Lys Leu His Leu Tyr Ser His Pro Ile Val Leu
225                 230                 235                 240

Gly Phe Arg Lys Ile Pro Met Gly Val Gly Leu Ser Pro Phe Leu Met
                245                 250                 255

Ala Gln Phe Thr Ser Ala Ile Cys Ser Val Val Arg Arg Ala Phe Pro
            260                 265                 270

His Cys Leu Ala Phe Ser Tyr Val Asp Asp Val Val Leu Gly Ala Lys
        275                 280                 285

Ser Val Gln His Arg Glu Ala Leu Tyr Thr Ala Val Thr Asn Phe Leu
    290                 295                 300

Leu Ser Leu Gly Ile His Leu Asn Pro Asn Lys Thr Lys Arg Trp Gly
305                 310                 315                 320

Tyr Ser Leu Asn Phe Leu Gly Tyr Ile Ile Gly Ser Trp Gly Thr Leu
                325                 330                 335

Pro Gln Asp His Ile Val Gln Lys Ile Lys His
            340                 345

<210> SEQ ID NO 17
<211> LENGTH: 310
<212> TYPE: PRT
<213> ORGANISM: Hep B virus

<400> SEQUENCE: 17

Phe Pro Pro Pro Ala Ser Thr Asn Arg Gln Ser Gly Arg Gln Pro Thr
1               5                   10                  15

Pro Ile Ser Pro Pro Leu Arg Asp Ser His Pro Gln Ala Met Gln Trp
            20                  25                  30

Asn Ser Thr Ala Phe His Gln Ala Leu Gln Asp Pro Arg Val Arg Gly
        35                  40                  45

Leu Tyr Leu Pro Ala Gly Gly Ser Ser Glu Thr Val Asn Pro Ala
50                  55                  60

Pro Asn Thr Ala Ser His Ile Ser Ser Ile Ser Ala Arg Thr Gly Asp
65                  70                  75                  80

Pro Val Thr Asn Met Glu Asn Ile Thr Ser Gly Leu Leu Gly Pro Leu
                85                  90                  95

Leu Val Leu Gln Ala Gly Phe Phe Leu Leu Thr Arg Ile Leu Thr Ile
            100                 105                 110

Pro Gln Ser Leu Asp Ser Trp Trp Thr Ser Leu Ser Phe Leu Gly Gly

```
            115                 120                 125
Ser Pro Val Cys Leu Gly Gln Asn Ser Gln Ser Pro Thr Ser Asn His
    130                 135                 140
Ser Pro Thr Ser Cys Pro Pro Thr Cys Pro Gly Tyr Arg Trp Met Cys
145                 150                 155                 160
Leu Arg His Phe Ile Ile Phe Leu Phe Ile Leu Leu Leu Cys Leu Ile
                165                 170                 175
Phe Leu Leu Val Leu Leu Asp Tyr Gln Gly Met Leu Pro Val Cys Pro
            180                 185                 190
Leu Ile Pro Gly Ser Pro Thr Thr Ser Thr Gly Pro Cys Lys Thr Cys
        195                 200                 205
Thr Thr Pro Ala Gln Gly Asn Ser Met Phe Pro Ser Cys Cys Cys Thr
    210                 215                 220
Lys Pro Thr Asp Gly Asn Cys Thr Cys Ile Pro Ile Pro Ser Ser Trp
225                 230                 235                 240
Ala Phe Ala Lys Tyr Leu Trp Glu Trp Ala Ser Val Arg Phe Ser Trp
                245                 250                 255
Leu Ser Leu Leu Val Pro Phe Val Gln Trp Phe Val Gly Leu Ser Pro
            260                 265                 270
Thr Val Trp Leu Ser Ala Met Trp Met Met Trp Tyr Trp Gly Pro Asn
        275                 280                 285
Leu Tyr Ser Thr Val Arg Pro Phe Ile Pro Leu Leu Pro Ile Phe Phe
    290                 295                 300
Cys Leu Trp Val Tyr Ile
305                 310

<210> SEQ ID NO 18
<211> LENGTH: 1016
<212> TYPE: DNA
<213> ORGANISM: Hep B virus

<400> SEQUENCE: 18
aatccgcctc ctgcctctac caatcgccag tcaggaaggc agcctacccc tcygactcca    60
cctttgagaa acactcatcc tcaggccatg yagtggaact ccacaaactt ccaccgaact   120
ctacaagatc ccagagtgaa aggcctgtat ctccctgctg gtggctccag ttcaggaaca   180
gtaaaccctg ttccgactac tgtctctcac acatcgtcaa tcttatcgag gattggggac   240
cctgcactga acatggagaa catcacatca ggattcctag gacccctgct cgcgttacag   300
gcggggtttt tctcgttgac aagaatcctc acaataccgc agagtctaga ctcgtggtgg   360
acttctctca attttctagg ggagaccacc gtgtgccttg gccaaaattc gcagtcccca   420
acctccaatc actcaccaac ctcctgtcct ccaacttgtc ctggttatcg ctggatgtgt   480
ctgcggcgtt ttatcatatt cctcttcatc ctgctgctat gcctcatctt cttgttggtt   540
cttctggact atcaaggtat gttgcccgtt gccctctaa ttccaggatc ctcaaccacc   600
agcacgggac catgcagaac ctgcacgtct cctgctcaaa ggaactctac gtatccctcc   660
tgttgctgta caaaaccttc ggacggaaat gcacctgta ttcccatccc atcatcctgg   720
gctttcggaa aattcctatg ggagtgggcc tcagcccgtt tctccttact cagtttacta   780
gtgccatttg ttcagtggtt cgtagggctt tcccccactg tttggctttc agttatatgg   840
atgatgtggt attggggggcc aggtctgtac agcatcgtga ggcccttttt accgctgtta   900
ccaattttct tttgtctctg ggtgtacatt taacccccgaa caaaacaaaa agatggggtt   960
actctttaca tttcctgggc tatgtcattg gatgttatgg gtcattgcca caagat      1016
```

```
<210> SEQ ID NO 19
<211> LENGTH: 338
<212> TYPE: PRT
<213> ORGANISM: Hep B virus
<220> FEATURE:
<221> NAME/KEY: MISC_FEATURE
<222> LOCATION: (30)..(30)
<223> OTHER INFORMATION: Xaa = any amino acid

<400> SEQUENCE: 19

Ser Ala Ser Cys Leu Tyr Gln Ser Pro Val Arg Lys Ala Ala Tyr Pro
1               5                   10                  15

Ser Asp Ser Thr Phe Glu Lys His Ser Ser Gly His Xaa Val Glu
            20                  25                  30

Leu His Lys Leu Pro Pro Asn Ser Thr Arg Ser Gln Ser Glu Arg Pro
            35                  40                  45

Val Ser Pro Cys Trp Trp Leu Gln Phe Arg Asn Ser Lys Pro Cys Ser
        50                  55                  60

Asp Tyr Cys Leu Ser His Ile Val Asn Leu Ile Glu Asp Trp Gly Pro
65                  70                  75                  80

Cys Thr Glu His Gly Glu His His Ile Arg Ile Pro Arg Thr Pro Ala
                85                  90                  95

Arg Val Thr Gly Gly Val Phe Leu Val Asp Lys Asn Pro His Asn Thr
            100                 105                 110

Ala Glu Ser Arg Leu Val Val Asp Phe Ser Gln Phe Ser Arg Gly Asp
        115                 120                 125

His Arg Val Pro Trp Pro Lys Phe Ala Val Pro Asn Leu Gln Ser Leu
    130                 135                 140

Thr Asn Leu Leu Ser Ser Asn Leu Ser Trp Leu Ser Leu Asp Val Ser
145                 150                 155                 160

Ala Ala Phe Tyr His Ile Pro Leu His Pro Ala Ala Met Pro His Leu
                165                 170                 175

Leu Val Gly Ser Ser Gly Leu Ser Arg Tyr Val Ala Arg Leu Pro Ser
            180                 185                 190

Asn Ser Arg Ile Leu Asn His Gln His Gly Thr Met Gln Asn Leu His
        195                 200                 205

Val Ser Cys Ser Lys Glu Leu Tyr Val Ser Leu Leu Leu Leu Tyr Lys
    210                 215                 220

Thr Phe Gly Arg Lys Leu His Leu Tyr Ser His Pro Ile Ile Leu Gly
225                 230                 235                 240

Phe Arg Lys Ile Pro Met Gly Val Gly Leu Ser Pro Phe Leu Leu Thr
                245                 250                 255

Gln Phe Thr Ser Ala Ile Cys Ser Val Val Arg Arg Ala Phe Pro His
            260                 265                 270

Cys Leu Ala Phe Ser Tyr Met Asp Asp Val Val Leu Gly Ala Arg Ser
        275                 280                 285

Val Gln His Arg Glu Ala Leu Phe Thr Ala Val Thr Asn Phe Leu Leu
    290                 295                 300

Ser Leu Gly Val His Leu Thr Pro Asn Lys Thr Lys Arg Trp Gly Tyr
305                 310                 315                 320

Ser Leu His Phe Leu Gly Tyr Val Ile Gly Cys Tyr Gly Ser Leu Pro
                325                 330                 335

Gln Asp
```

```
<210> SEQ ID NO 20
<211> LENGTH: 310
<212> TYPE: PRT
<213> ORGANISM: Hep B virus
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (31)..(31)
<223> OTHER INFORMATION: Xaa = any amino acid

<400> SEQUENCE: 20

Asn Pro Pro Ala Ser Thr Asn Arg Gln Ser Gly Arg Gln Pro Thr
1               5                   10                  15

Pro Xaa Thr Pro Pro Leu Arg Asn Thr His Pro Gln Ala Met Xaa Trp
            20                  25                  30

Asn Ser Thr Asn Phe His Arg Thr Leu Gln Asp Pro Arg Val Lys Gly
                35                  40                  45

Leu Tyr Leu Pro Ala Gly Gly Ser Ser Gly Thr Val Asn Pro Val
50                  55                  60

Pro Thr Thr Val Ser His Thr Ser Ser Ile Leu Ser Arg Ile Gly Asp
65                  70                  75                  80

Pro Ala Leu Asn Met Glu Asn Ile Thr Ser Gly Phe Leu Gly Pro Leu
                85                  90                  95

Leu Ala Leu Gln Ala Gly Phe Phe Ser Leu Thr Arg Ile Leu Thr Ile
                100                 105                 110

Pro Gln Ser Leu Asp Ser Trp Trp Thr Ser Leu Asn Phe Leu Gly Glu
                115                 120                 125

Thr Thr Val Cys Leu Gly Gln Asn Ser Gln Ser Pro Thr Ser Asn His
130                 135                 140

Ser Pro Thr Ser Cys Pro Pro Thr Cys Pro Gly Tyr Arg Trp Met Cys
145                 150                 155                 160

Leu Arg Arg Phe Ile Ile Phe Leu Phe Ile Leu Leu Leu Cys Leu Ile
                165                 170                 175

Phe Leu Leu Val Leu Leu Asp Tyr Gln Gly Met Leu Pro Val Cys Pro
                180                 185                 190

Leu Ile Pro Gly Ser Ser Thr Thr Ser Thr Gly Pro Cys Arg Thr Cys
                195                 200                 205

Thr Ser Pro Ala Gln Arg Asn Ser Thr Tyr Pro Ser Cys Cys Cys Thr
210                 215                 220

Lys Pro Ser Asp Gly Asn Cys Thr Cys Ile Pro Ile Pro Ser Ser Trp
225                 230                 235                 240

Ala Phe Gly Lys Phe Leu Trp Glu Trp Ala Ser Ala Arg Phe Ser Leu
                245                 250                 255

Leu Ser Leu Leu Val Pro Phe Val Gln Trp Phe Val Gly Leu Ser Pro
                260                 265                 270

Thr Val Trp Leu Ser Val Ile Trp Met Met Trp Tyr Trp Gly Pro Gly
                275                 280                 285

Leu Tyr Ser Ile Val Arg Pro Phe Leu Pro Leu Leu Pro Ile Phe Phe
                290                 295                 300

Cys Leu Trp Val Tyr Ile
305                 310
```

VARIANTS OF HEPATITIS B VIRUS WITH RESISTANCE TO ANTI-VIRAL NUCLEOSIDE AGENTS AND APPLICATIONS THEREOF

RELATED APPLICATIONS

This application is a Continuation of U.S. patent application Ser. No. 11/911,097 filed Oct. 9, 2007 which is the U.S., National Phase under 35 U.S.C. §371 of International Application PCT/AU2006/000450, filed Apr. 4, 2006 designating the U.S., and published in English as WO 2006/105597 on Oct. 12, 2006, which claims priority to Australian Patent Application No. 2005901757 filed Apr. 8, 2005 and Australian Patent Application No. 2005903972 filed Jul. 26, 2005, all of which are incorporated herein by reference in their entireties.

FIELD OF THE INVENTION

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. The present invention further contemplates assays for detecting such viral variants, which assays are useful in monitoring anti-viral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

DESCRIPTION OF THE PRIOR ART

Bibliographic details of the publications referred to in this specification are also collected at the end of the description.

The reference to any prior art in this specification is not, and should not be taken as, an acknowledgment or any form of suggestion that that prior art forms part of the common general knowledge in any country.

Hepatitis B virus (HBV) can cause debilitating disease conditions and can lead to acute liver failure. HBV is a DNA virus which replicates via an RNA intermediate and utilizes reverse transcription in its replication strategy (Summers and Mason, *Cell* 29: 403-415, 1982). The HBV genome is of a complex nature having a partially double-stranded DNA structure with overlapping open reading frames encoding surface, core, polymerase and X genes. The complex nature of the HBV genome is represented in FIG. 1. The polymerase consists of four functional regions, the terminal protein (TP), spacer, reverse transcriptase (rt) and ribonuclease (RNAse).

The polymerase gene of HBV overlaps the envelope gene, mutations in the catalytic domain of the polymerase gene can also affect the nucleotide and the deduced amino acid sequence of the envelope protein and vice versa. In particular, the genetic sequence for the neutralization domain of HBV known as the 'a' determinant, which is found within the HBsAg and located between amino acids 99 and 169, actually overlaps the major catalytic regions of the viral polymerase protein and in particular domains A and B.

The presence of an HBV DNA polymerase has led to the proposition that nucleoside or nucleotide analogs could act as effective anti-viral agents. Examples of nucleoside or nucleotide analogs currently being tested are penciclovir and its oral form (FCV) [Vere Hodge, *Antiviral Chem Chemother* 4: 67-84, 1993; Boyd et al., *Antiviral Chem Chemother.* 32: 358-363, 1987; Kruger et al., *Hepatology* 22: 219A, 1994; Main et al., *J. Viral Hepatitis* 3: 211-215, 1996], Lamivudine [(−)-β-2'-deoxy-3'-thiacytidine]; (3TC or LMV) [Severini et al., *Antimicrobial Agents Chemother.* 39: 430-435, 1995; Dienstag et al., *New England J Med* 333: 1657-1661, 1995]. New nucleoside or nucleotide analogs which have already progressed to clinical trials include the pyrimidines Emtricitabine, ((−)-β-L-2'-3'-dideoxy-5-fluoro-3'-thiacydidine; FTC), the 5-fluoro derivative of 3TC, and Clevudine (1-(2-fluoro-5-methyl-β-L-arabino-furanosyl) uracil; L-FMAU), a thymidine analog. Like 3TC, these are pyrimidine derivatives with an unnatural "L"-configuration. Several purine derivatives have also progressed to clinical trials; they include Entecavir (BMS-200, 475; ETV), a carbocyclic deoxyguanosine analog, diaminopurine dioxolane (DAPD), an oral pro-drug for dioxolane guanine ((−)-β-D-2-aminopurine dioxolane; DXG) and Adefovir dipivoxil, an oral prodrug for the acyclic deoxyadenosine monophosphate nucleoside or nucleotide analog Adefovir (9-[phosphonyl-methoxyethyl]-adenine; PMEA). Other drugs in pre-clinical and clinical trials include FLG [Medivir], ACH-126,443 (L-d4C) [Archillion Pharmaceuticals], ICN 2001-3 (ICN) and Racivir (RCV) [Pharmasett].

Whilst these agents are highly effective in inhibiting HBV DNA synthesis, there is the potential for resistant mutants of HBV to emerge during long term antiviral chemotherapy. In patients on prolonged LMV therapy, key resistance mutations are selected in the rt domain within the polymerase at rtM204I/V+/−rtL180M as well as other mutations. The nomenclature used for the polymerase mutations is in accordance with that proposed by Stuyver et al., 2001, supra. LMV is a nucleoside or a nucleotide analog that has been approved for use against chronic HBV infection. LMV is a particularly potent inhibitor of HBV replication and reduces HBV DNA titres in the sera of chronically infected patients after orthotopic liver transplantation (OLT) by inhibiting viral DNA synthesis. LMV monotherapy seems unlikely to be able to control HBV replication in the longer term. This is because emergence of LMV-resistant strains of HBV seems almost inevitable during monotherapy.

Adefovir dipivoxil (ADV: formerly, bis-pom PMEA) is an orally available prodrug of the acyclic deoxyadenosine monophosphate analog adefovir (formerly, PMEA) (FIG. 2). ADV is also a potent inhibitor of HBV replication and has recently been given FDA approval for use against chronic HBV infection. Adefovir dipivoxil differs from other agents in this class in that it is a nucleotide (vs. nucleoside) analog and as such bypasses the first phosphorylation reaction during drug activation. This step is often rate-limiting. Adefovir dipivoxil has demonstrated clinical activity against both wild-type and lamivudine-resistant strains of HBV and is currently in phase III clinical Testing (Gilson et al., *J Viral Hepat* 6: 387-395, 1999; Perrillo et al., *Hepatology* 32: 129-134, 2000; Peters et al., *Transplantation* 68: 1912-1914, 1999; Benhamou et al., *Lancet* 358: 718-723, 2001). During phase II studies a 30 mg daily dose of adefovir dipivoxil resulted in a mean 4 $\log_{10}$ decrease in viremia over 12 weeks (Heathcote et al., *Hepatology* 28: A620, 1998).

ADV is a substituted acyclic nucleoside phosphonate. This class of compounds also includes tenofovir disoproxil fumarate (also referred to as tenofovir DF, or tenofovir, or (TFV) or 9-R-(2-phosphonomethoxypropyl)adenine (PMPA) and is marketed as Viread by Gilead sciences).

TFV has antiviral activity against both HBV and HIV (Ying et al., *J Viral Hepat.* 7(2): 161-165, 2000; Ying et al., *J.*

*Viral Hepat.* 7(1): 79-83, 2000, 2000; Suo et al., *J Biol Chem.* 273(42): 27250-27258. 1998).

FTC has activity against HBV and HIV (Frick et al., *Antimicrob Agents Chemother* 37: 2285-2292, 1993).

Nucleoside or nucleotide analog therapy may be administered as monotherapy or combination therapy where two or more nucleoside or nucleotide analogs may be administered. The nucleoside or nucleotide analogs may also be administered in combination with other antiviral agents such as interferon or hepatitis B immunoglobulin (HBIG).

There is a need to monitor for the emergence of nucleoside/nucleotide-analog- or antibody-resistant strains of HBV and to develop diagnostic protocols to detect these resistant viruses and/or to use them to screen for and/or develop or design agents having properties making them useful as antiviral agents. Defective forms of these resistant strains or antigenic components therefrom are also proposed to be useful in the development of therapeutic vaccine compositions as are antibodies directed to viral surface components.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

Specific mutations in an amino acid sequence are represented herein as "$Xaa_1 nXaa_2$" where $Xaa_1$ is the original amino acid residue before mutation, n is the residue number and $Xaa_2$ is the mutant amino acid. The abbreviation "Xaa" may be the three letter or single letter (i.e. "X") code. An "rt" before "$Xaa_1 nXaa_2$" means "reverse transcriptase". An "s" means an envelope gene. The amino acid residues for HBV DNA polymerase are numbered with the residue methionine in the motif Tyr Met Asp Asp (YMDD) being residue number 204 (Stuyver et al, *Hepatology* 33: 751-757, 2001). The amino acid residues for hepatitis B virus surface antigen are number according to Norder et al. (*J. Gen. Virol.* 74: 341-1348, 1993). Both single and three letter abbreviations are used to define amino acid residues and these are summarized in Table 2.

In accordance with the present invention, the selection of HBV variants is identified in patients with chronic HBV infection treated with ADV and/or LMV. Consequently, HBV rt variants are contemplated which are resistant to, or which exhibit reduced sensitivity to, ADV, LMV, TFV or FTC; ADV and LMV; ADV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combinations thereof. Corresponding mutations in the surface antigen also occur. The identification of these HBV variants is important for the development of assays to monitor ADV, LMV, FTC and/or TFV resistance and/or resistance with ETV in combination with any nucleoside or nucleotide analog with the exception of LMV and/or resistance to other nucleoside or nucleotide analogs or other anti-HBV agents or combinations thereof and to screen for agents which are useful as alternative therapeutic agents. The subject variants are not proposed to exhibit resistance to ETV alone or ETV and LMV alone.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release.

The detection of such HBV variants is particularly important in the management of therapeutic protocols including the selection of appropriate agents for treating HBV infection. The method of this aspect of the present invention is predicated in part on monitoring the development in a subject of an increased HBV load in the presence of a nucleoside or nucleotide analog or other anti-HBV agents or combinations thereof. The clinician is then able to modify an existing treatment protocol or select an appropriate treatment protocol accordingly.

Accordingly, one aspect of the present invention is directed to an isolated Hepatitis B virus (HBV) variant wherein said variant comprises a nucleotide mutation in a gene encoding a DNA polymerase resulting in at least one amino acid addition, substitution and/or deletion to said DNA polymerase and wherein said variant exhibits decreased sensitivity to one or more nucleoside or nucleotide analogs selected from the list consisting of ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone. The variant HBV comprises a mutation in an overlapping open reading frame in its genome in a region defined by one or more of domains F and G and domain A through to E of HBV DNA polymerase.

Another aspect of the present invention provides an isolated HBV variant comprising a nucleotide mutation in the S gene resulting in at least one amino acid addition, substitution and/or deletion to the surface antigen and which exhibits decreased sensitivity to one or more nucleoside or nucleotide analogs selected from the list consisting of ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone.

Useful mutants in the rt region include, in one embodiment, mutations at codons rtN53, rtY54, rtL180, rtT181, rtT184, rtM204, rtN236, rtY124, rtH126, rtT128, rtS135, rtL180, rtS202, rtM204, rtH248, rtI53, rtS54, rtN122, rtM145, rtL180, rtM204, rtM250, rtN53, rtS85, rtS116, rtD134, rtN139, rtQ149, rtA181, rtS219, rtI233, rtN236 or rtM250. Particular mutants include rtN53, rtN53, rtY54, rtL180, rtT181, rtT184, rtM204, and rtN236, in another embodiment include rtY124, rtH126, rtT128, rtS135, rtL180, rtS202, rtM204, and rtH248, or yet another embodiment include rtI53, rtS54, rtN122, rtM145, rtL180, rtM204 and rtM250, or yet another embodiment rtN53, rtS85, rtS116, rtD134, rtN139, rtQ149, rtA181, rtS219, rtI233, rtN236, rtM250 or a combination thereof or an equivalent mutation. Even more particular mutants include rtN53K, rtN53K/N, rtY54D, rtL180M, rtT181A/V, rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or yet another embodiment rtN53D, rtS85A, rtS116P, rtD134V, rtN139E/K, rtQ149K, rtA181V, rtS219A, rtI233V, rtN236T, rtM250L or a combination thereof or an equivalent mutation.

Particularly useful mutants are at codons rtT184, rtS202, rtS219, rtI233, rtH248 or rtM250 such as rtT184S, rtS202C, rtS219A, rtI233V, rtH248N or rtM250L.

Useful mutations in the S gene include, in one embodiment include mutations at codons stT45, sL173, sL175, sI195, sT118, sP120, sP127, sI195, sT114, SI195, sS204, sI208, sS210, sVI4, sG130, sM133, sW172, sS204 or sS210 such as sT45K, sL173L/F, sL175F, sI195M, in another embodiment include sT118A, sP120T, sP127A and sI195M or yet another embodiment include sT114P, sI195M, sS204N, sI208T and sS210R and finally another embodiment include sV14A, sG130R, sM133T, sW172L, sS204G, sS210R.

The present invention further contemplates a method for determining the potential for an HBV to exhibit reduced sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof by isolating DNA or corresponding mRNA from the HBV and screening for a mutation in the nucleotide sequence encoding HBV DNA polymerase resulting in at least one amino acid substitution, deletion and/or addition in any one or more of domains F and G and domains A through to E or a region proximal thereto of the DNA polymerase and associated with resistance or decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone.

The presence of such a mutation is an indication of the likelihood of resistance to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

The present invention also provides a composition comprising a variant HBV resistant to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof or an HBV surface antigen from the variant HBV or a recombinant or derivative form thereof or its chemical equivalent and one or more pharmaceutically acceptable carriers and/or diluents. With the proviso that the HBV variant does not exhibit resistance to ETV alone or ETV or LMV alone.

Yet another aspect of the present invention provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof in the manufacture of a medicament for the treatment and/or prophylaxis of hepatitis B virus infection. With the proviso that the HBV variant does not exhibit resistance to ETV alone or ETV or LMV alone.

The present invention also contemplates a method for determining whether an HBV strain exhibits reduced sensitivity to a nucleoside or nucleotide analog or other anti-HBV agents or by isolating DNA or corresponding mRNA from the HBV and screening for a mutation in the nucleotide sequence encoding the DNA polymerase wherein the presence of the following mutations in the rt region: in one embodiment, mutations at codons rtN53, rtY54, rtL180, rtT181, rtT184, rtM204, rtN236, rtY124, rtH126, rtT128, rtS135, rtL180, rtS202, rtM204, rtH248, rtI53, rtS54, rtN122, rtM145, rtL180, rtM204, rtM250, rtN53, rtS85, rtS116, rtD134, rtN139, rtQ149, rtA181, rtS219, rtI233, rtN236 or rtM250. Particular mutants include rtN53, rtN53, rtY54, rtL180, rtT181, rtT184, rtM204, and rtN236, in another embodiment include rtY124, rtH126, rtT128, rtS135, rtL180, rtS202, rtM204, and rtH248, or yet another embodiment include rtI53, rtS54, rtN122, rtM145, rtL180, rtM204 and rtM250, or yet another embodiment rtN53, rtS85, rtS116, rtD134, rtN139, rtQ149, rtA181, rtS219, rtI233, rtN236, rtM250 or a combination thereof or an equivalent mutation. Even more particular mutants include rtN53K, rtN53K/N, rtY54D, rtL180M, rtT181A/V, rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or yet another embodiment rtN53D, rtS85A, rtS116P, rtD134V, rtN139E/K, rtQ149K, rtA181V, rtS219A, rtI233V, rtN236T, rtM250L or a combination thereof or an equivalent mutation. The mutations may also be a combination thereof or an equivalent mutation which mutation(s) is/are indicative of a variant which exhibits a decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone.

Still a further aspect provides a method for determining whether an HBV strain exhibits reduced sensitivity to a nucleoside or nucleotide analog said method comprising screening for a mutation in the nucleotide sequence encoding the envelope genes (s) wherein the presence of the following mutations in the s gene: in one embodiment include mutations at codons stT45, sL173, sL175, sI195, sT118, sP120, sP127, sI195, sT114, SI195, sS204, sI208, sS210, sV14, sG130, sM133, sW172, sS204 or sS210 such as sT45K, sL173L/F, sL175F, sI195M and in another embodiment include and sT118A, sP120T, sP127A and sI195M, or yet another embodiment include sT114P, sI195M, sS204N, sI208T, and sS210R, or still yet another embodiment include sV14A, sG130R, sM133T, sW172L, sS204G, sS210R or a combination thereof or an equivalent mutation or combinations thereof or an equivalent one or more other mutation is indicative of a variant which exhibits a decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and/or optionally other nucleoside or nucleotide analogs or other anti-HBV agents or combination thereof. With the proviso that the HBV variant does not exhibit resistance to ETV alone or ETV or LMV alone.

Preferably, the variants are in an isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions.

Another aspect of the present invention is directed to a variant HBV comprising a surface antigen having an amino acid sequence with a single or multiple amino acid substitution, addition and/or deletion or a truncation compared to a surface antigen from a reference or wild type HBV and wherein an antibody generated to the reference or wild type surface antigen exhibits an altered immunological profile relative to the HBV variant. One altered profile includes a reduced capacity for neutralizing the HBV. More particularly, the surface antigen of the variant HBV exhibits an altered immunological profile compared to a pre-treatment HBV where the variant HBV is selected for by a nucleoside or nucleotide analog or other anti-HBV agents of the HBV DNA polymerase. The variant HBV of this aspect of the invention may also comprise a nucleotide sequence comprising a single or multiple nucleotide substitution, addition and/or deletion compared to a pre-treatment HBV.

The present invention further contemplates a method for detecting a variant HBV exhibiting an altered immunological profile said method comprising isolating an HBV from a subject exposed to a nucleoside or nucleotide analog or combination of analogs selected from the listed consisting of ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting said HBV with a panel of one or more antibodies to a surface antigen and screening for any change in binding affinity or binding spectrum. With the proviso that the HBV variant does not exhibit resistance to ETV alone or ETV or LMV alone.

In a related invention, the present invention provides a method for detecting a variant HBV exhibiting an altered immunological profile said method comprising isolating a serum sample from a subject exposed to a nucleoside or nucleotide analog selected from the listed consisting of ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting the serum with a panel of HBV surface antigens or antibody-binding fragments thereof and screening for any change in binding affinity or binding spectrum. With the proviso that the HBV variant does not exhibit resistance to ETV alone or ETV or LMV alone.

The present invention extends to an isolated HBsAg or a recombinant form thereof or derivative or chemical equivalent thereof corresponding to the variant HBV. Generally, the HBsAg or its recombinant or derivative form or its chemical equivalent comprises an amino acid sequence with a single or multiple amino acid substitution, addition and/or deletion or a truncation compared to an HBsAg from a reference HBV and wherein an antibody directed to a reference HBV exhibits an altered immunological profile to an HBV carrying said variant HBsAg. In one embodiment, the altered immunological profile comprises a reduction in the ability to neutralize the variant HBV.

Another aspect of the present invention contemplates a method for detecting an agent which exhibits inhibitory activity to an HBV by generating a genetic construct comprising a replication competent-effective amount of the genome from the HBV contained in a plasmid vector and then transfecting said cells with said construct, contacting the cells, before, during and/or after transfection, with the agent to be tested, culturing the cells for a time and under conditions sufficient for the HBV to replicate, express genetic sequences and/or assemble and/or release virus or virus-like particles if resistant to said agents; and the subjecting the cells, cell lysates or culture supernatant fluid to viral- or viral-component-detection means to determine whether or not the virus has replicated, expressed genetic material and/or assembled and/or been released in the presence of the agent. In a preferred embodiment, the plasmid vector in a baculovirus vector and the method comprises generating a genetic construct comprising a replication competent-effective amount of the genome from the HBV contained in or fused to an amount of a baculovirus genome effective to infect cells and then infecting said cells with said construct, contacting the cells, before, during and/or after infection, with the agent to be tested, culturing the cells for a time and under conditions sufficient for the HBV to replicate, express genetic sequences and/or assemble and/or release virus or virus-like particles if resistant to said agent and then subjecting the cells, cell lysates or culture supernatant fluid to viral- or viral-component-detection means to determine whether or not the virus has replicated, expressed genetic material and/or assembled and/or been released in the presence of the agent.

In connection with these methods, the plasmid vector may include genes encoding part or all of other viral vectors such as baculovirus vectors or adenovirus vectors (see Ren and Nassal, *J. Virol.* 75(3). 1104-1116, 2001).

In an alternative embodiment, the method comprises generating a continuous cell line comprising an infectious copy of the genome of the HBV in a replication competent effective amount such that said infectious HBV genome is stably integrated into said continuous cell line such as but not limited to the 2.2.15 or AD cell line, contacting the cells with the agent to be tested, culturing the cells for a time and under conditions sufficient for the HBV to replicate, express genetic sequences and/or assemble and/or release virus or virus-like particles if resistant to the agent and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al., *Antimicrob Agents Chemother.* 46(4): 1005-1013, 2002; Xiong et al., *Hepatology.* 28(6): 1669-73, 1998). The HBV polymerase may be a wild-type or reference HBV polymerase or mutant HBV polymerase.

The identification of viral variants enables the production of vaccines comprising particular recombinant viral components such as polymerases or envelope genes PreS1, PreS2, S encoding for L, M, S proteins as well as therapeutic vaccines comprising defective HBV variants. Rational drug design may also be employed to identify or generate therapeutic molecules capable of interacting with a polymerase or envelope genes PreS1, PreS2, S encoding for L, M, S proteins or other component of the HBV. Such drugs may also have diagnostic potential. In addition, defective HBV variants may also be used as therapeutic compositions to generate an immune response against the same, similar or homologous viruses. Alternatively, antibodies generated to the HBV variants or surface components thereof may be used in passive immunization of subjects against infection by HBV variants or similar or homologous viruses. Furthermore, agents such as nucleoside or nucleotide analogs, RNAi or siRNA molecules (both DNA-derived or synthetic), antisense or sense oligonucleotides, chemical or proteinaceous molecules having an ability to down-regulate the activity of a component of HBV and inhibit replication, maintenance, infection, assembly or release are contemplated by the present invention.

As indicated above, the present invention does not extend to an HBV variant exhibiting resistance or reduced sensitivity to ETV alone or ETV and LMV alone.

A summary of the abbreviations used throughout the subject specification are provided in Table 3.

A summary of sequence identifiers used throughout the subject specification is provided in Table 1.

TABLE 1

Summary of sequence identifiers

| SEQUENCE ID NO: | DESCRIPTION |
| --- | --- |
| 1 | PCR primer |
| 2 | PCR primer |
| 3 | PCR primer |
| 4 | PCR primer |
| 5 | PCR primer |
| 6 | Nucleotide sequence of catalytic region of polymerase from resistant HBV Patient A: Sample A |
| 7 | Deduced amino acid sequence of catalytic region of polymerase resistant HBV Patient A: Sample A |
| 8 | Dededuced amino acid sequence of envelope gene from resistant HBV from Pateint A: Sample A |
| 9 | Nucleotide sequence of catalytic region of polymerase from resistant HBV Patient A: Sample B |
| 10 | Dededuced amino acid sequence of envelope gene from resistant HBV from Pateint A: Sample B |
| 11 | Dededuced amino acid sequence of envelope gene from resistant HBV from Pateint A: Sample B |
| 12 | Nucleotide sequence of catalytic region of polymerase from resistant HBV Patient B |
| 13 | Deduced amino acid sequence of catalytic region of polymerase resistant HBV Patient B |
| 14 | Dededuced amino acid sequence of envelope gene from resistant HBV from Pateint B |
| 15 | Nucleotide sequence of catalytic region of polymerase from resistant HBV Patient C |

TABLE 1-continued

Summary of sequence identifiers

| SEQUENCE ID NO: | DESCRIPTION |
|---|---|
| 16 | Deduced amino acid sequence of catalytic region of polymerase resistant HBV Patient C |
| 17 | Dedecuded amino acid sequence of envelope gene from resistant HBV from Pateint C |
| 18 | Nucleotide sequence of catalytic region of polymerase from resistant HBV Patient D |
| 19 | Deduced amino acid sequence of catalytic region of polymerase resistant HBV Patient D |
| 20 | Dedecuded amino acid sequence of envelope gene from resistant HBV from Pateint D |

TABLE 2

Single and three letter amino acid abbreviations

| Amino Acid | Three-letter Abbreviation | One-letter symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |
| Valine | Val | V |
| Any residue | Xaa | X |

TABLE 3

Abbreviations

| ABBREVIATION | DESCRIPTION |
|---|---|
| 3TC | (LMV); (-)-β-2'-deoxy-3'-thiacytidine |
| ADV | adefovir dipivoxil |
| DAPD | diaminopurine dioxalone |
| DXG | dioxolane guanine |
| ETV | entecavir |
| FAM | famciclovir |
| FCV | famciclovir |
| FTC | emtricitabine |
| HBIG | hepatitis B immunoglobulin |
| HBsAg | hepatitis B surface antigen |
| HBV | hepatitis B virus |
| LMV | lamividuine |
| PMEA | 9-[phosphonyl-methoxyethyl]-adenine; adefovir |
| PMPA | 9-R-(2-phosphonomethoxypropyl)adenine |
| RNase | ribonuclease |
| rt ("rt" before "Xaa₁nXaa₂" means reverse transcriptase) | reverse transcriptase |
| s (as used in a mutation, e.g. sF134V) | envelope gene |
| TFV | tenofovir disoproxil fumarate |
| YMDD | Tyr Met Asp Asp-a motif in the polymerase protein; where the Met residue is |

TABLE 3-continued

Abbreviations

| ABBREVIATION | DESCRIPTION |
|---|---|
| | designated residue number 204 of the reverse transcriptase |

BRIEF DESCRIPTION OF THE FIGURES

FIG. 3 is a representation showing comparison of the HBV nucleotide sequence encoding the catalytic region of the polymerase gene in sequential samples from Patient A during ADV treatment (sample A).

FIG. 4 is a representation showing comparison of the deduced amino acid sequence of the catalytic region of the polymerase gene in sequential samples from Patient A during ADV therapy (sample A).

FIG. 5 is a representation showing comparison of the deduced amino acid sequence of the envelope gene in sequential samples from Patient A during ADV therapy (sample A).

FIG. 6 is a representation showing comparison of the HBV nucleotide sequence encoding the catalytic region of the polymerase gene in sequential samples from Patient A during ADV treatment (sample B).

FIG. 7 is a representation showing comparison of the deduced amino acid sequence of the catalytic region of the polymerase gene in sequential samples from Patient A during ADV therapy (sample B).

FIG. 8 is a representation showing comparison of the deduced amino acid sequence of the envelope gene in sequential samples from Patient A during ADV therapy (sample B).

FIG. 9 is a representation showing comparison of the HBV nucleotide sequence encoding the catalytic region of the polymerase gene in sequential samples from Patient B during ADV and LMV treatment.

FIG. 10 is a representation showing comparison of the deduced amino acid sequence of the catalytic region of the polymerase gene in sequential samples from Patient B during ADV and LMV therapy.

FIG. 11 is a representation showing comparison of the deduced amino acid sequence of the envelope gene in sequential samples from Patient B during ADV and LMV therapy.

FIG. 12 is a representation the HBV nucleotide sequence encoding the catalytic region of the polymerase gene in samples from Patient C during ADV treatment.

FIG. 13 is a representation the deduced amino acid sequence of the catalytic region of the polymerase gene in samples from Patient C during ADV therapy.

FIG. 14 is a representation the deduced amino acid sequence of the envelope gene in samples from Patient C during ADV therapy.

FIG. 15 is a graphical representation of increase in HBV DNA levels (viral load) and ALT over time (days since the initiation of the first antiviral therapy).

FIG. 16 is a representation the HBV nucleotide sequence encoding the catalytic region of the polymerase gene in samples from Patient D during ADV and LMV treatment.

FIG. 17 is a representation the deduced amino acid sequence of the catalytic region of the polymerase gene in samples from Patient D during ADV and LMV therapy.

DETAILED DESCRIPTION OF THE INVENTION

Figure 1:
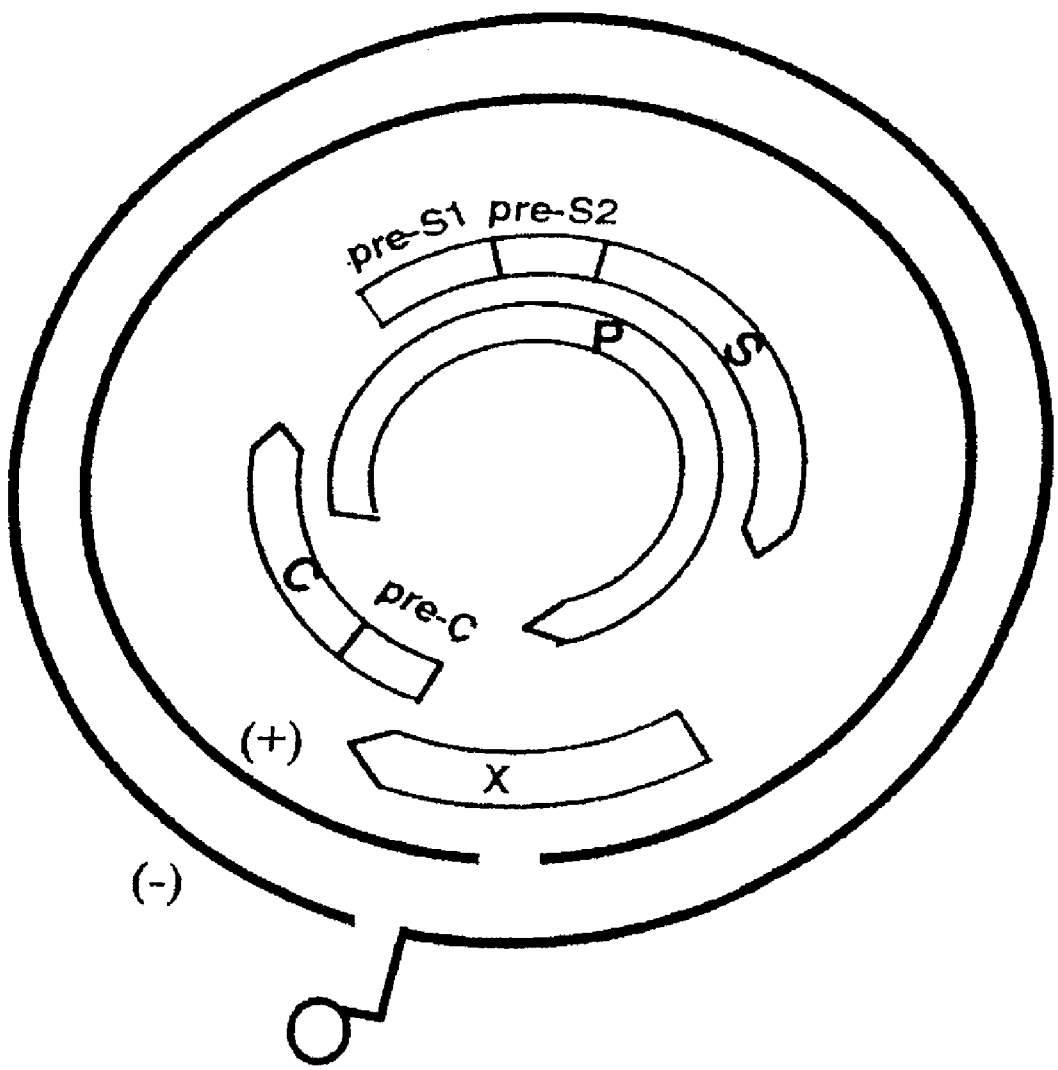
FIG. 1 is a diagrammatic representation showing the partially double stranded DNA HBV genome showing the overlapping open reading frames encoding surface (S), core (C), polymerase (P) and X gene.

The present invention is predicated in part on the identification and isolation of nucleoside or nucleotide analog-resistant variants of HBV following treatment of patients with either ADV or LMV or ETV or more particularly ADV and LMV or TFV and LMV, or ETV and optionally one or more other nucleoside analogs or nucleotide analogs or other anti-HBV agents such as TFV or FTC. In particular, ADV or ADV and LMV or ETV treated patients gave rise to variants of HBV exhibiting decreased or reduced sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone. Reference herein to "decreased" or "reduced" in relation to sensitivity to ADV and/or LMV and/or FTC and/or TFV and/or ETV includes and encompasses a complete or substantial resistance to the nucleoside or nucleotide analog or other anti-HBV agents as well as partial resistance and includes a replication rate or replication efficiency which is more than a wild-type in the presence of a nucleoside or nucleotide analog or other anti-HBV agents. In one aspect, this is conveniently measured by an increase in viral load during treatment, or alternatively, there is no substantial decrease in HBV DNA viral load from pre-treatment HBV DNA levels during treatment (i.e., non-response to treatment).

Accordingly, one aspect of the present invention provides an isolated hepatitis B virus (HBV) variant wherein said variant comprises a nucleotide mutation resulting in an amino acid addition, substitution and/or deletion in a protein encoded by said variant and wherein said variant exhibits decreased sensitivity to one or more nucleoside or nucleotide analogs selected from the list consisting of ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; and ADV and FTC and LMV and TFV and ETV.

In particular, the mutations are in the DNA polymerase or surface antigen (S gene product).

Accordingly, one aspect of the present invention contemplates an isolated Hepatitis B virus (HBV) variant wherein said variant comprises a nucleotide mutation in a gene encoding a DNA polymerase resulting in at least one amino acid addition, substitution and/or deletion to said DNA polymerase and wherein said variant exhibits decreased sensitivity to one or more nucleoside or nucleotide analogs selected from the list consisting of ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

A further aspect of the present invention provides a method for determining the potential for an HBV to exhibit reduced sensitivity to a nucleoside or nucleotide analog selected from ADV, LMV, TFV and FTC or ETV and another analog except LMV or a combination thereof or optionally other nucleoside or nucleotide analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of ADV, LMV, TFV, FTC and/or wherein the presence of such a mutation is an indication of the likelihood of resistance to said one or more of ADV, LMV, TFV and/or FTC and/or ETV and another nucleoside or nucleotide analog except LMV.

Before describing the present invention in detail, it is to be understood that unless otherwise indicated, the subject invention is not limited to specific formulations of components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "a nucleoside or nucleotide analog" includes a single analog, as well as two or more analogs; reference to "an HBV variant" includes reference to two or more HBV variants; and so forth.

In describing and claiming the present invention, the following terminology is used in accordance with the definitions set forth below.

The terms "analog", "compound", "active agent", "pharmacologically active agent", "medicament", "active" and "drug" are used interchangeably herein to refer to a chemical compound that induces a desired effect such as inhibit viral replication, infection, maintenance, assembly and/or the function of an enzyme such as HBV DNA polymerase. The terms also encompass pharmaceutically acceptable and pharmacologically active ingredients of those active agents specifically mentioned herein including but not limited to salts, esters, amides, prodrugs, active metabolites, analogs and the like. When the terms "analog", "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

The present invention contemplates, therefore, compounds useful in inhibiting HBV replication, infection, maintenance, assembly and/or the function of an enzyme such as HBV DNA polymerase. Reference to an "analog", "compound", "active agent", "pharmacologically active agent", "medicament", "active" and "drug" such as ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. A "combination" also includes a two-part or more such as a multi-part anti-HBV therapeutic composition where the agents are provided separately and given or dispensed separately or admixed together prior to dispensation.

The terms "effective amount" and "therapeutically effective amount" of an agent as used herein mean a sufficient amount of the agent to provide the desired therapeutic or physiological effect of inhibiting HBV replication, infection, maintenance, assembly and/or the function of an enzyme such as HBV DNA polymerase. Furthermore, an "effective HBV-inhibiting amount" or "effective symptom-ameliorating amount" of an agent is a sufficient amount of the agent to directly or indirectly inhibit replication, infection, maintenance, assembly and/or the function of an enzyme such as HBV DNA polymerase. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage in relation to HBV infection. Thus, for example, "treating" a patient involves prevention of HBV infection as well as treatment of a clinically HBV symptomatic individual by inhibiting HBV replication, infection, maintenance, assembly and/or the function of an enzyme such as HBV DNA polymerase. Thus, for example, the present method of "treating" a patient with HBV infection or with a propensity for one to develop encompasses both prevention of HBV infection as well as treating HBV infection or symptoms thereof. In any event, the present invention contemplates the treatment or prophylaxis of HBV infection.

"Patient" as used herein refers to an animal, preferably a mammal and more preferably a primate including a lower primate and even more preferably, a human who can benefit from the formulations and methods of the present invention. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an "animal" includes an avian species such as a poultry bird (including ducks, chicken, turkeys and geese), an aviary bird or game bird. The condition in a non-human animal may not be a naturally occurring HBV infection but HBV-like infection may be induced.

As indicated above, the preferred animals are humans, non-human primates such as marmossets, baboons, orangatangs, lower primates such as tupia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

An "anti-HBV agent" includes a nucleoside or nucleotide analog, protein, chemical compound, RNA or DNA or RNAi or siRNA oligonucleotide (either DNA-derived or synthetic).

Preferably, the decreased sensitivity is in respect of ETV. Alternatively, the decreased sensitivity is in respect of ADV or LMV. Alternatively, the decreased sensitivity is in respect of TFV. Alternatively, the decreased sensitivity is in respect of FTC. Alternatively, the decreased sensitivity is in respect of ETV and another nucleotide or nucleoside analog with the exception of LMV alone. Alternatively, the decreased sensitivity is in respect of ADV and TFV and optionally ETV. Alternatively, the decreased sensitivity is in respect of LMV and TFV and optionally ETV. Alternatively, the decreased sensitivity is in respect of ADV and FTC and optionally ETV. Alternatively, the decreased sensitivity is in respect to FTC and TFV and optionally ETV. Alternatively, the decreased sensitivity is in respect of FTC and LMV and optionally ETV. Alternatively, the decreased sensitivity is in respect of ADV and LMV and TFV and optionally ETV. Alternatively, the decreased sensitivity is in respect to ADV and TFV and FTC and optionally ETV. Alternatively, the decreased sensitivity is in respect to LMV and TFV and FTC and optionally ETV. Alternatively, the decrease sensitivity is in respect of ADV and LMV and FTC and optionally ETV. Alternatively, the decreased sensitivity is in respect of ADV and FTC and TFV and LMV and optionally ETV. The present invention does not extend to an HBV variant exhibiting resistance or reduced sensitivity to ETV alone or ETV and LMV alone.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release. Reference herein to "nucleic acid" includes reference to a sense or antisense molecule, RNA or DNA, oligonucleotides and RNAi and siRNA molecules and complexes containing same.

In addition to a mutation in the gene encoding DNA polymerase, due to the overlapping nature of the HBV genome (FIG. 1), a corresponding mutation may also occur in the gene encoding the S gene encoding the surface antigen (HBsAg) resulting in reduced interactivity of immunological reagents such as antibodies and immune cells to HBsAg. The reduction in the interactivity of immunological reagents to a viral surface component generally includes the absence of immunological memory to recognize or substantially recognize the viral surface component. The present invention extends, therefore, to an HBV variant exhibiting decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof or a reduced interactivity of an immunological reagent to HBsAg wherein the variant is selected for following ADV and/or LMV combination or sequential treatment. The term "sequential" in this respect means ADV followed by LMV and/or TFV and/or ETV, and/or FTC, LMV followed by ADV and/or TFV and/or FTC and/or ETV or ETV followed by one or more of ADV, FTC, LMV and/or TFV, or multiple sequential administrations of each of ETV, ADV, LMV and/or TFV and/or FTC. With the proviso that the HBV variant does not exhibit resistance to ETV alone or ETV or LMV alone.

A viral variant may, therefore, carry A mutation only in the DNA polymerase gene or both in the DNA polymerase gene and the S gene. The term "mutation" is to be read in its broadest context and includes multiple mutations.

The present invention extends to a mutation and any domain of the HBV DNA polymerase and in particular regions F and G, and domains A through to E provided said mutation leads to decreased sensitivity to ADV and/or LMV and/or TFV and/or ETV and/or FTC or combinations thereof.

In this specification, reference is particularly made to the conserved regions of the DNA polymerase as defined by domains A to E. Regions A to E are defined by the amino acid sequence set forth in Formula II in Australian Patent No. 734831.

Preferably, the mutation results in an altered amino acid sequence in any one or more of domains F and G, and domains A through to E or regions proximal thereto of the HBV DNA polymerase.

Another aspect of the present invention provides an HBV variant comprising a mutation in an overlapping open reading frame in its genome wherein said mutation is in a region defined by one or more of domains F and G, and domains A through to E of HBV DNA polymerase and wherein said variant exhibits decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone.

Another preferred aspect of the present invention contemplates an HBV variant comprising a mutation in the nucleotide sequence encoding HBsAg resulting in an amino acid addition, substitution and/or deletion in said HBsAg wherein said variant exhibits decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone.

More particularly, the present invention provides a variant HBV comprising a surface antigen having an amino acid sequence with a single or multiple amino acid substitution, addition and/or deletion or a truncation compared to a surface antigen from a reference or wild-type HBV and wherein an antibody generated to the reference or wild-type surface antigen exhibits reduced capacity for neutralizing said HBV variant, said variant selected by exposure of a subject to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone.

The term "combination therapy" means that both combinations of ADV, LMV, FTC, TFV, and/or ETV are co-administered in the same composition or simultaneously in separate compositions. The term "sequential therapy" means that the two agents are administered within seconds, minutes, hours, days or weeks of each other and in either order. Sequential therapy also encompasses completing a therapeutic course with one or other of ADV, LMV, FTC, TFV or ETV and then completing a second or third or subsequent therapeutic courses with the other of ADV, LMV, FTC, TFV or ETV.

Accordingly, another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV therapy or therapy by one or more other nucleoside or nucleotide analogs or other anti-HBV agents.

Yet still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ETV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and LMV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and TFV therapy or therapy by one or more other nucleoside or nucleotide analogs or other anti-HBV agents.

Yet still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and ETV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and TFV therapy or therapy by one or more other nucleoside or nucleotide analogs or other anti-HBV agents.

Yet a further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and ETV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and FTC therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and FTC therapy or therapy by one or more other nucleoside or nucleotide analogs or other anti-HBV agents.

Still another aspect another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and ETV therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and LMV therapy or therapy by one or more other nucleoside or nucleotide analogs or other anti-HBV agents.

Even another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and ETV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV and/or ETV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV and/or ETV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and FTC and/or ETV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC, LMV and TFV and/or ETV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, FTC and TFV and/or ETV therapy or therapy by one or more other nucleoside or nucleotide analogs or other anti-HBV agents.

Still yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV, FTC and TFV and/or ETV therapy or therapy by one or more other nucleoside or nucleotide analogs or other anti-HBV agents.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. Furthermore, the present invention provides isolated components from the variant HBVs such as but not limited to an isolated HBsAg. Accordingly, the present invention provides an isolated HBsAg or a recombinant form thereof or derivative or chemical equivalent thereof, said HBsAg being from a variant HBV selected by exposure of a subject to one or more of ADV, LMV, FTC, TFV and/or ETV or optionally one or more nucleoside or nucleotide analogs or other anti-HBV agents.

More particularly, yet another aspect of the present invention is directed to an isolated variant HBsAg or a recombinant or derivative form thereof or a chemical equivalent thereof wherein said HBsAg or its recombinant or derivative form or its chemical equivalent exhibits an altered immunological profile compared to an HBsAg from a reference HBV, said HBsAg being from a variant HBV selected by exposure of a subject to one or more of ADV, LMV, FTC, TFV and/or ETV or optionally one or more nucleoside or nucleotide analogs or other anti-HBV agents.

Even more particularly, the present invention provides an isolated variant HBsAg or a recombinant or derivative form thereof or a chemical equivalent thereof wherein said HBsAg or its recombinant or derivative form or its chemical equivalent comprises an amino acid sequence with a single or multiple amino acid substitution, addition and/or deletion or a truncation compared to an HBsAg from a reference HBV and wherein a neutralizing antibody directed to a reference HBV exhibits no or reduced neutralising activity to an HBV carrying said variant HBsAg, said HBsAg being from a variant HBV selected by exposure of a subject to one or more of ADV, LMV, FTC, TFV and/or ETV or optionally one or more nucleoside or nucleotide analogs or other anti-HBV agents.

Preferred mutations in the HBV DNA polymerase include variants selected from patients with HBV recurrence following ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. Nucleoside or nucleotide analogs or other anti-HBV agents may be indicated during, after or prior to a transplantation procedure (e.g. bone marrow transplantation (BMT) or OLT) or following treatment of patients diagnosed with hepatitis. Following selection of variants, viral loads are obtainable at levels similar to pre-treatment levels or increase while on therapy.

Useful mutants in the rt region include, in one embodiment, mutations at codons rtN53, rtY54, rtL180, rtT181, rtT184, rtM204, rtN236, rtY124, rtH126, rtT128, rtS135, rtL180, rtS202, rtM204, rtH248, rtI53, rtS54, rtN122, rtM145, rtL180, rtM204, rtM250, rtN53, rtS85, rtS116, rtD134, rtN139, rtQ149, rtA181, rtS219, rtI233, rtN236 or rtM250 such as rtN53K, rtN53K/N, rtY54D, rtL180M, rtT181A/V rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or still yet another embodiment include rtN53D, rtS85A, rtS116P, rtD134V, rtN139E/K, rtQ149K, rtA181V, rtS219A, rtI233V, rtN236T, rtM250L or a combination thereof or an equivalent mutation. Particularly useful mutants are rtT184S, rtS202C, rtS219A, rtI233V, rtH248N or rtM250L Such HBV variants are proposed to exhibit a decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof. It should be noted that the nomenclature system for amino acid positions is based on the methionine residues in the YMDD motif being designated codon rtM204. This numbering system is different to that in Australian Patent No. 734831 where the methionine residue in the YMDD motif within the polymerase gene is designated codon 550. In this regard, rtL180M and rtM204V correspond to L526M and M550V, respectively, in Australian Patent No. 734831. Corresponding mutations may also occur in envelope genes such as in one or more of PreS1, PreS2 and S.

Another potential mode of action of ADV and other acyclic nucleoside phosphonates is that of immune stimulation (Calio et al., *Antiviral Res.* 23: 77-89, 1994). A number of mutations resulted in changes in the envelope gene detected in HBV variants which may be associated with immune escape. These changes include in one embodiment include in one embodiment include mutations at codons stT45, sL173, sL175, sI195, sT118, sP120, sP127, sI195, sT114, SI195, sS204, sI208, sS210, sV14, sG130, sM133, sW172, sS204 or sS210 such as sT45K, sL173L/F, sL175F, sI195M and in another embodiment include and sT118A, sP120T, sP127A and sI195M, or yet another embodiment include sT114P, sI195M, sS204N, sI208T, and sS210R, or still yet another embodiment include sV14A, sG130R, sM133T, sW172L, sS204G, sS210R or a combination thereof or an equivalent mutation, or a combination thereof or an equivalent mutation.

The identification of the variants of the present invention permits the generation of a range of assays to detect such variants. The detection of such variants may be important in identifying resistant variants to determine the appropriate form of chemotherapy and/or to monitor vaccination protocols, or develop new or modified vaccine preparations.

Still another aspect of the present invention contemplates a method for determining the potential for an HBV to exhibit reduced sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and A domains through to E or a region proximal thereto of said DNA polymerase and associated with resistance or decreased sensitivity to ADV, LMV, TFV, or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone.

Accordingly, another aspect of the present invention provides a method for determining the potential for an HBV to exhibit reduced sensitivity to a nucleoside or nucleotide analog selected from ADV, LMV, TFV and FTC and ETV and another nucleotide or nucleoside analog except LMV alone or optionally other nucleoside or nucleotide analogs, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and A through E or a region proximal thereto of said DNA polymerase and associated with resistance or decreases sensitivity to one or more of ADV, LMV, TFV, FTC and/or ETV wherein the presence of such a mutation is an indication of the likelihood of resistance to said one or more of ADV, LMV, TFV and/or FTC and/or ETV and another analog except LMV alone. With the proviso that the HBV variant does not exhibit resistance to ETV alone or ETV or LMV alone.

Preferably, the assay detects one or more mutations at codons rtN53, rtY54, rtL180, rtT181, rtT184, rtM204, rtN236, rtY124, rtH126, rtT128, rtS135, rtL180, rtS202, rtM204, rtH248, rtI53, rtS54, rtN122, rtM145, rtL180, rtM204, rtM250, rtN53, rtS85, rtS116, rtD134, rtN139, rtQ149, rtA181, rtS219, rtI233, rtN236 or rtM250 such as rtN53K, rtN53K/N, rtY54D, rtL180M, rtT181A/V rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or still yet another embodiment include rtN53D, rtS85A, rtS116P, rtD134V, rtN139E/K, rtQ149K, rtA181V, rtS219A, rtI233V, rtN236T, rtM250L, or a combination thereof or an equivalent mutation is indicative of a variant wherein said variant exhibits a decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof.

Accordingly, another aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment include mutations at codons stT45, sL173, sL175, sI195, sT118, sP120, sP127, sI195, sT114, SI195, sS204, sI208, sS210, sV14, sG130, sM133, sW172, sS204 or sS210 such as sT45K, sL173L/F, sL175F, sI195M and in another embodiment include and sT118A, sP120T, sP127A and sI195M, or yet another embodiment include sT114P, sI195M, sS204N, sI208T, and sS210R, or still yet another embodiment include sV14A, sG130R, sM133T, sW172L, sS204G, sS210R or a combination thereof or an equivalent mutation, in even still another embodiment, rtN53K, rtN53K/N, rtY54D, rtL180M, rtT181A/V rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or still yet another embodiment include rtN53D, rtS85A, rtS116P, rtD134V, rtN139E/K, rtQ149K, rtA181V, rtS219A, rtI233V, rtN236T, rtM250L or a combination thereof or an equivalent mutation, or combinations thereof or an equivalent one or more other mutation is indicative of a variant which exhibits a decreased sensitivity to ADV, LMV, TFV or FTC; ADV and LMV; ADV and TFV; LMV and TFV; FTC and ADV; FTC and TFV; FTC and LMV; ETV and ADV; ETV and LMV; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

A further aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment, mutations at codons stT45, sL173, sL175, sI195, sT118, sP120, sP127, sI195, sT114, SI195, sS204, sI208, sS210, sV14, sG130, sM133, sW172, sS204 or sS210 such as sT45K, sL173L/F, sL175F, sI195M and in another embodiment include and sT118A, sP120T, sP127A and sI195M, or yet another embodiment include sT114P, sI195M, sS204N, sI208T, and sS210R, or still yet another embodiment include sV14A, sG130R, sM133T, sW172L, sS204G, sS210R or a combination thereof or an equivalent mutation, in even still another embodiment, rtN53K, rtN53K/N, rtY54D, rtL180M, rtT181A/V rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or still yet another embodiment include rtN53D, rtS85A, rtS116P, rtD134V, rtN139E/K, rtQ149K, rtA181V, rtS219A, rtI233V, rtN236T, rtM250L or a combination thereof or an equivalent mutation, combinations thereof or an equivalent one or more other mutation is indicative of a variant which exhibits a decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof.

The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

One particularly useful nucleic acid detection system is the reverse hybridization technique. In this technique, DNA from an HBV sample is amplified using a biotin or other ligand-labeled primer to generate a labeled amplificon. Oligonucleotides immobilized to a solid support such as a nitrocellulose film are then used to capture amplified DNA by hybridization. Specific nucleic acid fragments are identified via biotin or the ligand. Generally, the labeled primer is specific for a particular nucleotide variation to be detected. Amplification occurs only if the variation to be detected is present. There are many forms of the reverse hybridization assay and all are encompassed by the present invention.

Another aspect contemplated by the present invention provides a method for detecting a variant HBV exhibiting an altered immunological profile said method comprising isolating an HBV from a subject exposed to a nucleoside or nucleotide analog selected from the listed consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting said HBV with a panel of one or more antibodies to a surface antigen and screening for any change in binding affinity or binding spectrum.

In a related embodiment, the present invention contemplates a method for detecting a variant HBV exhibiting an altered immunological profile said method comprising isolating a serum sample from a subject exposed to a nucleoside or nucleotide analog selected from the listed consisting of ADV, LMV, TFV, ETV or FTC; ADV and LMV; ADV and TFV; LMV and TFV; FTC and ADV; FTC and TFV; FTC and LMV; ETV and ADV; ETV and LMV; ETV and FTC; ETV and TFV; ADV and LMV and TFV; or ADV and FTC and TFV; TFV and FTC and LMV; ADV and LMV and ETV; ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, and then contacting the serum with a panel of HBV surface antigens or antibody-binding fragments thereof and screening for any change in binding affinity or binding spectrum.

Detecting HBV replication in cell culture is particularly useful.

This and other aspects of the present invention is particularly amenable to microarray analysis such as to identify oligonucleotides including sense and antisense molecules, RNAi or siRNA molecules or DNA or RNA-binding molecules which down-regulate genomic sequences or transcripts of HBV. Microarray analysis may also be used to identify particular mutations in the HBV genome such as within the HBV DNA polymerase-coding region or the HBsAg-coding region.

Another aspect of the present invention contemplates a method for detecting an agent which exhibits inhibitory activity to an HBV by:
  generating a genetic construct comprising a replication competent-effective amount of the genome from the HBV contained in a plasmid vector and then transfecting said cells with said construct;
  contacting the cells, before, during and/or after transfection, with the agent to be tested;
  culturing the cells for a time and under conditions sufficient for the HBV to replicate, express genetic sequences and/or assemble and/or release virus or virus-like particles if resistant to said agents; and
  then subjecting the cells, cell lysates or culture supernatant fluid to viral- or viral-component-detection means to determine whether or not the virus has replicated, expressed genetic material and/or assembled and/or been released in the presence of the agent.

In a preferred embodiment, the plasmid vector may include genes encoding part or all of other viral vectors such as baculovirus or adenovirus (Ren and Nassal, 2001, supra) and the method comprises:
  generating a genetic construct comprising a replication competent-effective amount of the genome from the HBV contained in or fused to an amount of a baculovirus genome or adenovirus genome effective to infect cells and then infecting said cells with said construct;
  contacting the cells, before, during and/or after infection, with the agent to be tested;
  culturing the cells for a time and under conditions sufficient for the HBV to replicate, express genetic sequences and/or assemble and/or release virus or virus-like particles if resistant to said agent; and
  then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the method comprises:
  generating a continuous cell line comprising an infectious copy of the genome of the HBV in a replication competent effective amount such that said infectious HBV genome is stably integrated into said continuous cell line such as but not limited to 2.2.15 or AD;
  contacting the cells with the agent to be tested;
  culturing the cells for a time and under conditions sufficient for the HBV to replicate, express genetic sequences and/or assemble and/or release virus or virus-like particles if resistant to the agent; and
  then subjecting the cells, cell lysates or culture supernatant fluid to viral- or viral-component-detection means to determine whether or not the virus has replicated, expressed genetic material and/or assembled and/or been released in the presence of the agent.

The above-mentioned methods are particularly useful in identifying or developing agents against HBV variants such as those carrying mutations, in one embodiment, mutations at codons rtN53, rtY54, rtL180, rtT181, rtT184, rtM204, rtN236, rtY124, rtH126, rtT128, rtS135, rtL180, rtS202, rtM204, rtH248, rtI53, rtS54, rtN122, rtM145, rtL180, rtM204, rtM250, rtN53, rtS85, rtS116, rtD134, rtN139, rtQ149, rtA181, rtS219, rtI233, rtN236 or rtM250 such as rtN53K, rtN53K/N, rtY54D, rtL180M, rtT181A/V rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or still yet another embodiment include rtN53D, rtS85A, rtS116P, rtD134V, rtN139E/K, rtQ149K, rtA181V, rtS219A, rtI233V, rtN236T, rtM250L or a combination thereof or an equivalent mutation, or a combination thereof or an equivalent mutation; in a further embodiment, mutations at codons stT45, sL173, sL175, sI195, sT118, sP120, sP127, sI195, sT114, SI195, sS204, sI208, sS210, sV14, sG130, sM133, sW172, sS204 or sS210 such as sT45K, sL173L/F, sL175F, sI195M and in another embodiment include and sT118A, sP120T, sP127A and sI195M, or yet another embodiment include sT114P, sI195M, sS204N, sI208T, and sS210R, or still yet another embodiment include sV14A, sG130R, sM133T, sW172L, sS204G, sS210R or a combination thereof or an equivalent mutation.

Accordingly, another aspect of the present invention contemplates a method for determining whether an HBV strain exhibits reduced sensitivity to a nucleoside or nucleotide analog or other potential anti-HBV agent, said method comprising isolating DNA or corresponding mRNA from said HBV and screening for a mutation in the nucleotide sequence of the envelope genes or DNA polymerase gene selected from, in one embodiment, in one embodiment, mutations at codons rtN53, rtY54, rtL180, rtT181, rtT184, rtM204, rtN236, rtY124, rtH126, rtT128, rtS135, rtL180, rtS202, rtM204, rtH248, rtI53, rtS54, rtN122, rtM145, rtL180, rtM204, rtM250, rtN53, rtS85, rtS116, rtD134, rtN139, rtQ149, rtA181, rtS219, rtI233, rtN236 or rtM250 such as rtN53K, rtN53K/N, rtY54D, rtL180M, rtT181A/V rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or still yet another embodiment include rtN53D, rtS85A, rtS116P, rtD134V, rtN139E/K, rtQ149K, rtA181V, rtS219A, rtI233V, rtN236T, rtM250L, or a combination thereof or an equivalent mutation, or a combination thereof or an equivalent mutation; in a further embodiment, mutations at codons stT45, sL173, sL175, sI195, sT118, sP120, sP127, sI195, sT114, SI195, sS204, sI208, sS210, sV14, sG130, sM133, sW172, sS204 or sS210 such as sT45K, sL173L/F, sL175F, sI195M and in another embodiment include and sT118A, sP120T, sP127A and sI195M, or yet another embodiment include sT114P, sI195M, sS204N, sI208T, and sS210R, or still yet another embodiment include sV14A, sG130R, sM133T, sW172L, sS204G, sS210R or a combination thereof or an equivalent mutation and/or optionally other nucleoside or nucleotide analogs or other anti-HBV agents or combination thereof.

The detection of amino acid variants of DNA polymerase is conveniently accomplished by a range of amino acid detection techniques. Where an HBV variant comprises an amino acid change, then such an isolate is considered a putative HBV variant having an altered DNA polymerase activity.

The present invention further contemplates agents which inhibit HBV variants resistant to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof resistant HBV variants. Such agents are particularly useful if long term treatment by ADV, LMV, FTC, TFV and/or ETV and/or optionally other nucleoside or nucleotide analogs such as TFV is contemplated by the clinician. The agents may be DNA or RNA or proteinaceous or non-proteinaceous chemical molecules. Natural product screening such as from plants, coral and microorganisms is also contemplated as a useful potential source of masking agents as is the screening of combinatorial or chemical libraries. The agents may be in isolated form or in the form of a pharmaceutical composition or formulation and may be administered in place of or sequentially or simultaneously with a nucleoside or nucleotide analog. Furthermore, rationale drug design is contemplated including solving the crystal or NMR structure of, for example, HBV DNA polymerase and designing agents which can bind to the enzyme's active site. This approach may also be adapted to other HBV components.

Accordingly, another aspect of the present invention contemplates a method for detecting an agent which exhibits inhibitory activity to an HBV which exhibits resistance or decreased sensitivity ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, said method comprising:

generating a genetic construct comprising a replication competent-effective amount of the genome from said HBV contained in a plasmid vector and then transfecting said cells with said construct;

contacting said cells, before, during and/or after transfection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Still another aspect of the present invention provides a method for detecting an agent which exhibits inhibitory activity to an HBV which exhibits resistance or decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, said method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Preferably, the HBV genome is stably integrated into the cells' genome.

Particularly useful cells are 2.2.15 cells (Price et al., *Proc. Natl. Acad. Sci. USA* 86(21). 8541-8544, 1989 or AD cells (also known as HepAD32 cells or HepAD79 cells [Ying et al, 2000 Supra].

Whilst the baculovirus vector is a particularly useful in the practice of the present invention, the subject invention extends to a range of other vectors such as but not limited to adenoviral vectors.

The present invention further extends to cell lines (e.g. 2.2.15 or AD cells) carrying genetic constructs comprising all or a portion of an HBV genome or a gene or part of a gene therefrom.

The present invention also provides for the use of the subject HBV variants to screen for anti-viral agents. These anti-viral agents inhibit the virus. The term "inhibit" includes antagonizing or otherwise preventing infection, replication, assembly and/or release or any intermediate step. Preferred anti-viral agents include nucleoside or nucleotide analogs or anti-HBV agents, however, the present invention extends to non-nucleoside molecules.

In addition, rational drug design is also contemplated to identify or generate chemical molecules which either mimic a nucleoside or which interact with a particular nucleotide sequence or a particular nucleotide. Combinatorial chemistry and two hybrid screening are some of a number of techniques which can be employed to identify potential therapeutic or diagnostic agents.

In one example, the crystal structure or the NMR structure of polymerase or the surface antigen is used to rationally design small chemical molecules likely to interact with key regions of the molecule required for function and/or antigenicity. Such agents may be useful as inhibitors of polymerase activity and/or may alter an epitope on the surface antigen.

Several models of the HBV polymerase have been prepared due to the similarity with reverse transcriptase from HIV (Das et al., *J. Virol* 75(10): 4771-4779, 2001; Bartholomeusz et al., *Intervirology* 40(5-6): 337-342 1997; Allen et al., *Hepatology* 27(6): 1670-1677, 1998). The models of the HBV polymerase can be used for the rational drug design of new agents effective against HBV encoding the resistant mutations as well as wild type virus. The rational drug that is designed may be based on a modification of an existing anti-viral agent such as the agent used in the selection of the HBV encoding the mutations associated with resistance. Viruses or clones expressing HBV genomic material encoding the mutations may also be used to screen for new antiviral agents.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al., *Antimicrob Agents Chemother.* 46(4): 1005-1013, 2002; Xiong et al., *Hepatology* 28(6). 1669-1673, 1998).

As indicated above, microarray technology is also a useful means of identifying agents which are capable of interacting with defined HBV internal or external components. For example, arrays of HBV DNA polymerase or peptide fragments thereof carrying different amino acid variants may be used to screen for agents which are capable of binding or otherwise interacting with these molecules. This is a convenient way of determining the differential binding patterns of agents between HBV variants. Arrays of antibodies may also be used to screen for altered HBsAg molecules. Microarrays are also useful in proteomic analysis to identify molecules such as antibodies, interferons or cytokines which have an ability to interact with an HBV component. Microarrays of DNA and RNA molecules may also be employed to identify sense and antisense molecules for genetic regions on the HBV genome or transcripts thereof.

The above methods are particularly useful in identifying an inhibitor of an HBV resistant to or exhibiting reduced sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof. The present invention extends, therefore, to compositions of the inhibitors. The inhibitors may also be in the form of antibodies or genetic molecules such as ribozymes, antisense molecules and/or sense molecules for co-suppression or the induction of RNAi or may be other nucleoside or nucleotide analogs or other anti-HBV agents or derivatives of known analogs. Reference to RNAi includes reference to short, interfering RNAs (siRNA) and all RNAi-type molecules may be DNA-derived or synthetic.

The term "composition" includes a "pharmaceutical composition" or a formulation.

The inhibitor is referred to below as an "active ingredient" or "active compound" and may be selected from the list of inhibitors given above.

The composition may include an antigenic component of the HBV, a defective HBV variant or an agent identified through natural product screening or rational drug design (including combinatorial chemistry).

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical composition may also comprise genetic molecules such as a vector capable of transfecting target cells where the vector carries a nucleic acid molecule capable of encoding an aspartyl protease inhibitor. The vector may, for example, be a viral vector.

Pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and a flavouring. Of course, any material used in preparing any dosage unit form should be pharmaceutically pure and substantially non-toxic in the amounts employed. In addition, the active compound(s) may be incorporated into sustained-release preparations and formulations.

As stated above, the present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Yet another aspect of the present invention provides a composition comprising a variant HBV resistant to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or an HBV surface antigen from said variant HBV or a recombinant or derivative form thereof or its chemical equivalent and one or more pharmaceutically acceptable carriers and/or diluents. Such a composition may be regarded as a therapeutic composition and is useful in generating an immune response including a humoral response. Generally, the HBV variants are "defective" and in themselves are unable to cause a sustained infection in a subject.

As indicated above, antibodies may be generated to the mutant HBV agents and used for passive or direct vaccination against infection by these viruses. The antibodies may be generated in humans or non-human animals. In the case of the latter, the non-human antibodies may need to be deimmunized or more specifically humanized prior to use. Deimmunized may include, for example, grafting complimentarity determining regions (CDRs) from the variable region of a murine or non-human animal anti-HBV antibody onto a human consensus fragment antibody binding (Fab) polypeptide. Alternatively, amino acids defining epitopes in the variable region of the antibody may be mutated so that the epitopes are no longer recognized by the human MHC II complex.

Insofar as ribozyme, antisense or co-suppression (RNAi) or siRNA or complexes thereof repression is concerned, this is conveniently aimed at post-transcription gene silencing. DNA or RNA may be administered or a complex comprising RNAi or a chemical analog thereof specific for HBV mRNA may be employed.

All such molecules may be incorporated into pharmaceutical compositions.

In another embodiment, the present invention provides a biological composition comprising a variant HBV or an HBsAg or L, M or S proteins from said variant HBV or a recombinant or derivative form thereof or its chemical equivalent.

Generally, if an HBV is used, it is first attenuated. The biological composition according to this aspect of the present invention generally further comprises one or more pharmaceutically acceptable carriers and/or diluents.

The biological composition may comprise HBsAg or like molecule from one HBV variant or the composition may be a cocktail of HbsAgs or L, M or S proteins or like molecules from a range of ADV- and/or LMV- and/or, FTC- and/or TFV-resistant HBV variants. Similar inclusions apply where the composition comprises an HBV.

The present invention is further directed to the use of defective HBV variants in the manufacture of therapeutic vaccines to vaccinate individuals against infection by HBV strains having a particular nucleotide sequence or encoding a particular polymerase or surface antigen or L, M or S proteins.

Examples of suitable vaccine candidates are defective forms of HBV variants comprising a mutation selected from, in one embodiment, in one embodiment, mutations at codons rtN53, rtY54, rtL180, rtT181, rtT184, rtM204, rtN236, rtY124, rtH126, rtT128, rtS135, rtL180, rtS202, rtM204, rtH248, rtI53, rtS54, rtN122, rtM145, rtL180, rtM204, rtM250, rtN53, rtS85, rtS116, rtD134, rtN139, rtQ149, rtA181, rtS219, rtI233, rtN236 or rtM250 such as rtN53K, rtN53K/N, rtY54D, rtL180M, rtT181A/V rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or still yet another embodiment include rtN53D, rtS85A, rtS116P, rtD134V, rtN139E/K, rtQ149K, rtA181V, rtS219A, rtI233V, rtN236T, rtM250L or a combination thereof or an equivalent mutation, or a combination thereof or an equivalent mutation; in a further embodiment, mutations at codons stT45, sL173, sL175, sI195, sT118, sP120, sP127, sI195, sT114, SI195, sS204, sI208, sS210, sV114, sG130, sM133, sW172, sS204 or sS210 such as sT45K, sL173L/F, sL175F, sI195M and in another embodiment include and sT118A, sP120T, sP127A and sI195M, or yet another embodiment include sT114P, sI195M, sS204N, sI208T, and sS210R, or still yet another embodiment include sV14A, sG130R, sM133T, sW172L, sS204G, sS210R or a combination thereof or an equivalent mutation.

In one embodiment, for example, an HBV variant may be identified having a particular mutation in its polymerase conferring resistance or decreased sensitivity to a nucleoside or nucleotide analog. This variant may then be mutated to render it defective, i.e. attenuated or unable to cause infection. Such a defective, nucleoside or nucleotide analog-resistant virus may then be used as a therapeutic vaccine against virulent viruses having the same mutation in its polymerase.

The subject invention extends to kits for assays for variant HBV resistant to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

Still another aspect of the present invention contemplates a method for determining the potential for an HBV to exhibit reduced sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof and/or optionally other nucleoside or nucleotide analogs or other anti-HBV agents or combination thereof, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and domains A through to E or a region proximal thereto of said DNA polymerase and associated with resistance or decreased sensitivity to ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof, wherein the presence of such a mutation is an indication of the likelihood of resistance to said ADV, LMV, TFV or FTC; ADV and LMV; ADV and TFV; LMV and TFV; FTC and ADV; FTC and TFV; FTC and LMV; ETV and ADV; ETV and FTC; ETV and TFV; ADV and LMV and TFV; or ADV and FTC and TFV; TFV and FTC and LMV; ADV and LMV and ETV, ADV and ETV and TFV; ETV and LMV and TFV; ADV and LMV and FTC; ADV and FTC and LMV and TFV; ETV and FTC and LMV and TFV; ADV and ETV and LMV and TFV; ADV and FTC and ETV and TFV; ADV and FTC and LMV and ETV; or ADV and FTC and LMV and TFV and ETV and/or optionally other nucleoside or nucleotide analogs or other anti-HBV agents or combinations thereof. With the proviso that the HBV variant does not exhibit resistance to ETV alone or ETV or LMV alone.

An assessment of a potential viral variant is important for selection of an appropriate therapeutic protocol. Such an assessment is suitably facilitated with the assistance of a computer programmed with software, which inter alia adds input codes for at least two features associated with the viral variants to provide a value corresponding to the resistance or sensitivity of a viral variant to a particular chemical compound or immunological agent. The value can be selected from (a) the ability to exhibit resistance for reduced sensitivity to a particular compound or immunological agent; (b) an altered DNA polymerase from wild-type HBV; (c) an altered surface antigen from wild-type HBV; or (d) morbidity or recovery potential of a patient. Thus, in accordance with the present invention, the values for such features are stored in a machine-readable storage medium, which is capable of processing the data to provide a value for a particular viral variant or a biological specimen comprising same.

Thus, in another aspect, the invention contemplates a computer program product for assessing the likely usefulness of a viral variant or biological sample comprising same for determining an appropriate therapeutic protocol in a subject (FIG. 15), said product comprising:

(1) code that receives as input code for at least two features associated with said viral agents or biological sample comprising same, wherein said features are selected from:
   (a) the ability to exhibit resistance for reduced sensitivity to a particular compound or immunological agent;
   (b) an altered DNA polymerase from wild-type HBV;
   (c) an altered surface antigen from wild-type HBV; or
   (d) morbidity or recovery potential of a patient;
(2) code that adds said input code to provide a sum corresponding to a value for said viral variants or biological samples; and
(3) a computer readable medium that stores the codes.

In a related aspect, the invention extends to a computer for assessing the likely usefulness of a viral variant or biological sample comprising same in a subject, wherein said computer comprises:

(1) a machine-readable data storage medium comprising a data storage material encoded with machine-readable data, wherein said machine-readable data comprise input codes for at least two features associated with said viral variant or biological sample; wherein said features are selected from:—
   (a) the ability to exhibit resistance for reduced sensitivity to a particular compound or immunological agent;
   (b) an altered DNA polymerase from wild-type HBV;
   (c) an altered surface antigen from wild-type HBV; or
   (d) morbidity or recovery potential of a patient;
(2) a working memory for storing instructions for processing said machine-readable data;

(3) a central-processing unit coupled to said working memory and to said machine-readable data storage medium, for processing said machine readable data to provide a sum of said input code corresponding to a value for said compound(s); and (4) an output hardware coupled to said central processing unit, for receiving said value.

Any general or special purpose computer system is contemplated by the present invention and includes a processor in electrical communication with both a memory and at least one input/output device, such as a terminal. FIG. 15 shows a generally suitable computer system. Such a system may include, but is not limited to, personal computers, workstations or mainframes. The processor may be a general purpose processor or microprocessor or a specialized processor executing programs located in RAM memory. The programs may be placed in RAM from a storage device, such as a disk or pre-programmed ROM memory. The RAM memory in one embodiment is used both for data storage and program execution. The computer system also embraces systems where the processor and memory reside in different physical entities but which are in electrical communication by means of a network.

In an alternative embodiment, the program screens for a mutation selected from, in one embodiment, in one embodiment, mutations at codons rtN53, rtY54, rtL180, rtT181, rtT184, rtM204, rtN236, rtY124, rtH126, rtT128, rtS135, rtL180, rtS202, rtM204, rtH248, rtI53, rtS54, rtN122, rtM145, rtL180, rtM204, rtM250, rtN53, rtS85, rtS116, rtD134, rtN139, rtQ149, rtA181, rtS219, rtI233, rtN236 or rtM250 such as rtN53K, rtN53K/N, rtY54D, rtL180M, rtT181A/V rtT184S, rtM204V, and rtN236T, in another embodiment include rtY124H, rtH126R, rtT128N, rtS135C, rtL180M rtS202C rtM204V, and rtH248N, or yet another embodiment include rtI53V, rtS54T, rtN122T, rtM145L, rtL180M, rtM204V and rtM250L, or still yet another embodiment include rtN53D, rtS85A, rtS116P, rtD134V, rtN139E/K, rtQ149K, rtA181V, rtS219A, rtI233V, rtN236T, rtM250L or a combination thereof or an equivalent mutation or a combination thereof or an equivalent mutation; in a further embodiment, mutations at codons stT45, sL173, sL175, sI195, sT118, sP120, sP127, sI195, sT114, SI195, sS204, sI208, sS210, sV14, sG130, sM133, sW172, sS204 or sS210 such as sT45K, sL173L/F, sL175F, sI195M and in another embodiment include and sT118A, sP120T, sP127A and sI195M, or yet another embodiment include sT114P, sI195M, sS204N, sI208T, and sS210R, or still yet another embodiment include sV14A, sG130R, sM133T, sW172L, sS204G, sS210R or a combination thereof or an equivalent mutation.

The present invention is further described by the following non-limiting Examples.

Example 1

Overlapping Genome of HBV

The overlapping genome of HBV is represented in FIG. 1. The gene encoding DNA polymerase (P), overlaps the viral envelope genes, Pre-S1 and Pre-S2, and partially overlaps the X and core (C) genes. The HBV envelope comprises small, middle and large proteins HBV surface antigens. The large protein component is referred to as the HBV surface antigen (HBsAg) and is encoded by the S gene sequence. The Pre-S1 and Pre-S2 gene sequences encode the other envelope components.

Example 2

Patients on ADV Treatment and Analysis of HBV DNA

Patient A: During ADV treatment, unique HBV mutations were detected by PCR amplification sequencing using the methods described in Example 4; (Table 4). There was an evolution in the quasspecies detected. The mutation profile initially selected on ADV (sample A) includes the unique mutations at rtN53K, rtY54D, rtL180M, rtT184S, and rtM204V. A key unique mutation is rtT184S. Subsequently, a different ADV resistance profile was detected in sample B rtN53K/N, rtL180M, rtT181A/V, and rtN236T. Key unique mutations are rtT181A/V, and rtN236T detected previously in ADV resistant patients (Table 4, FIGS. 3, 4, 5 6, 7 and 8).

The changes in the HBsAg include sT45K, sL175F, sI195M in sample A and in the subsequent sample B sT45K and sL173L/F were detected. These unique changes were compared to reference sequences from each of the eight genotypes A-H as well as a consensus sequence from pretreatment samples to determine unique changes Patient B: The HBV mutations during ADV treatment are listed in Table 5 and FIGS. 9, 10, and 11. Key unique changes in the rt region of the HBV DNA polymerase include rtS202C and rtH248N. Other changes in the HBV polymerase while on ADV treatment include rtY124H, rtH126R, rtT128N, rtS135C, rtL180M and rtM204V. The changes in the HBsAg while on ADV treatment include sT118A, sP120T, sP127A and sI195M.

Patient C: The HBV mutations during ADV treatment are listed in Table 6 and FIGS. 12, 13, and 14. The key unique change in the rt region of the HBV DNA polymerase included rtM250L. Other unique changes in the HBV polymerase while on ADV treatment include rtI53V, rtS54T, rtN122T, rtM145L, rtL180M and rtM204V. The changes in the HBsAg while on ADV treatment include sT114P, sI195M, sS204N, sI208T, and sS210R.

Figure 18:
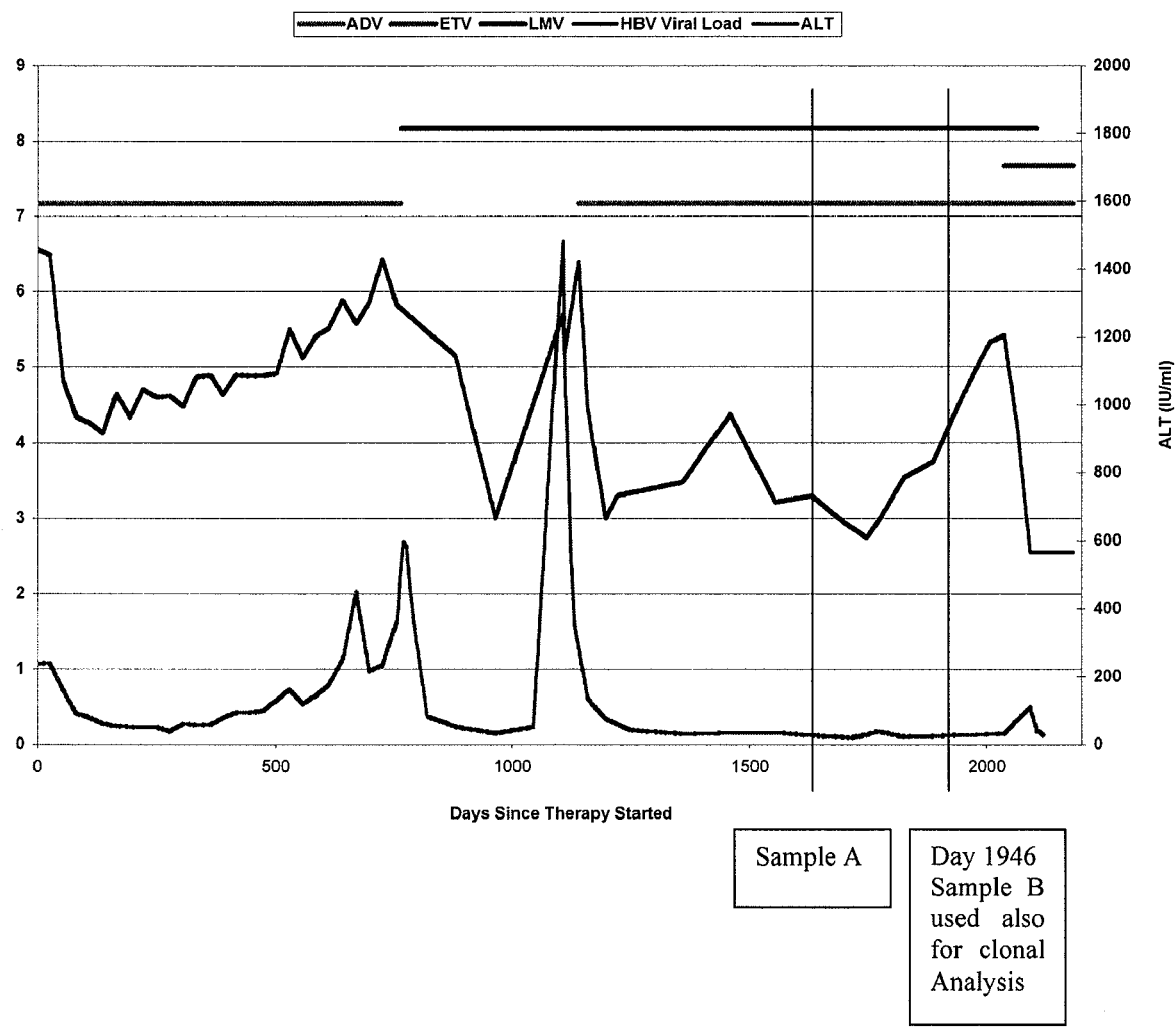
FIG. 18 is a representation the deduced amino acid sequence of the envelope gene in samples from Patient D during ADV and LMV therapy.

Patient D: This patient had initially selected ADV resistant mutations at rtN236T (Angus et al., *Gastroenterology.* 125 (2):292-7. 2003). This patient was subsequently treated with ADV and LMV. There was a virological breakthrough during the combination antiviral therapy (refer to FIG. 15 for a graphical representation of increase in HBV DNA levels (viral load) and ALT over time (days since the initiation of the first antiviral therapy). The HBV mutations during dual ADV and LMV treatment are listed in Table 7 and FIGS. 16, 17 and 18. By PCR amplification of the HBV genome and direct sequencing the unique changes in the rt region of the HBV DNA polymerase include, rtD134V, rtN139E/K, rtI233V, rtM250L. These occurred in association with the known ADV resistant mutations at rtA181V and rtN236T. The key unique mutations include rtI233V and rtM250L. All unique changes in the HBV polymerase while on ADV And LMV treatment include rtN53D, rtS116P, rtD134V, rtN139E, rtA181V, rtS219A, rtI233V, rtN236T, rtM250L. Clonal analysis was performed on a PCR amplified product encoding the polymerase genes, from HBV isolated at the time of virological breakthrough (see Example 15). A further key mutations were detected in this PCR amplified product at rtS85A other mutations at rtN139K/E and rtQ149K were also detected as minor species (Table 7 footnote).

The changes in the HBsAg while on ADV and LMV treatment include sV14A, sG130R, sM133T, sW172L, sS204G, sS210R.

Example 3

Detection of Viral Markers

Hepatitis B surface antigen (HBsAg), hepatitis B e antigen (HBeAg), anti-HBe and hepatitis B core antigen (HBcAg) specific IgG and IgM were measured using commercially available immunoassays (Abbott Laboratories, North Chicago, Ill., USA). Hepatitis B viral DNA levels were measured using a capture hybridization assay according to the manufacturer's directions (Digene Hybrid Capture II, Digene Diagnostics Inc., Beltsville, Md.). The manufacturers stated cut-off for detecting HBV viremia in clinical specimens was $0.7 \times 10^6$ copies/ml or 2.5 pg/ml [Hendricks et al., *Am J Clin Pathol* 104: 537-46, 1995]. HBV DNA levels can also be quantitated using other commercial kits such as Cobas amplification HBV monitor kit (Roche).

Example 4

Sequencing of HBV DNA

HBV DNA was extracted from 100 µl of serum as described previously by Aye et al., *J. Hepatol.* 26: 1148-1153, 1997. Oligonucleotides were synthesized by Geneworks, Adelaide, Australia. Amplification of the HBV polymerase gene or the entire HBV genome has been described by Aye et al., 1997, supra and Ayres et al., *Methods Mol Med.* 95:125-49, 2004.

The specific amplified products were purified using PCR purification columns such as from MO BIO Laboratories Inc (La Jolla, Calif.) and directly sequenced using Big Dye terminator Cycle sequencing Ready Reaction Kit (Perkin Elmer, Cetus Norwalk, Conn.). The PCR primers were used as sequencing primers, OS1 5'-GCC TCA TTT TGT GGG TCA CCA TA-3' (nt 1408-1430) [SEQ ID NO:1], TTA3 5'-AAA TTC GCA GTC CCC AAA-3'(nt2128-2145) [SEQ ID NO:2], JM 5'-TTG GGG TGG AGC CCT CAG GCT-3' (nt1676-1696) [SEQ ID NO:3], TTA4 5'-GAA AAT TGG TAA CAG CGG-3' (nt 2615-2632) [SEQ ID NO:4], OS2 5' TCT CTG ACA TAC TTT CCA AT 3' (nt 2798-2817) [SEQ ID NO:5], to sequence the internal regions of the PCR products.

Example 5

Adefovir Dipivoxil (ADV)

Figure 2:
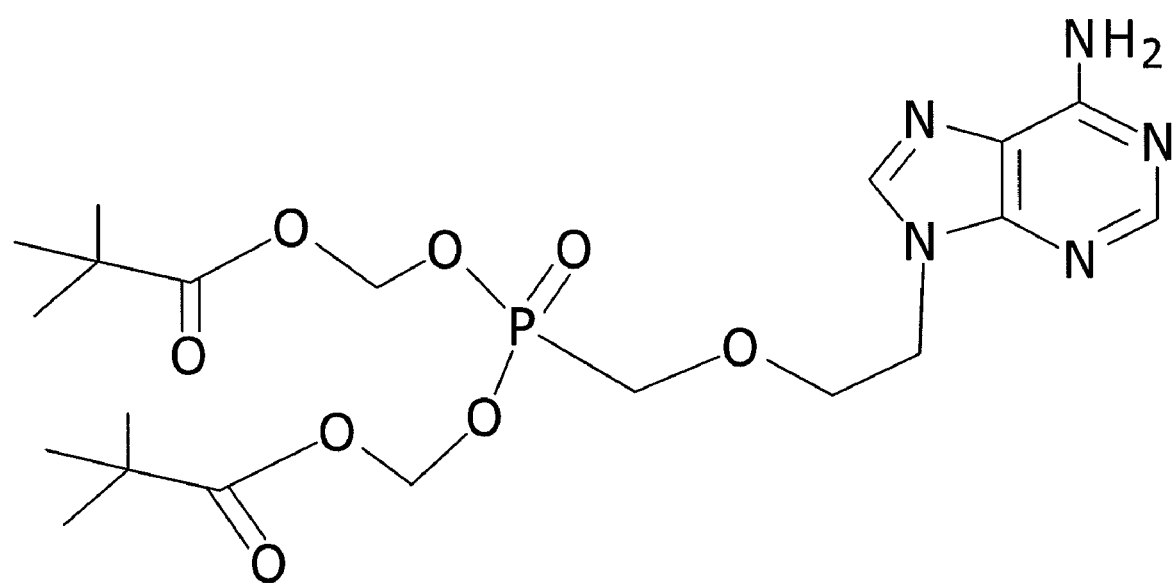
FIG. 2 is a diagrammatic representation of the chemical structure of ADV.

ADV (formerly Bis-pom PMEA)) is a potent inhibitor of HBV replication. The structure of ADV is shown in FIG. 2 and its synthesis is described by Benzaria et al., *J Med. Chem.* 39: 4958-4965, 1996).

Example 6

In Vitro Analysis of Antiviral Resistance

The sensitivity/resistance profile of HBV mutants to adefovir, tenofovir and other antiviral agents was examined in vitro using recombinant HBV/baculovirus. The procedure for analysing the resistance profile is outlined in the following Examples 7-14.

Example 7

Cell Culture

Sf21 insect cells were maintained in supplemented Grace's insect medium further supplemented with 10% v/v heat-inactivated fetal bovine serum (Gibco BRL, Gaithersburg, Md.) in humidified incubator at 28 C with $CO_2$. HepG2 cells were maintained in minimal essential medium supplemented with 10% v/v heat-inactivated fetal bovine serum (MEM-FBS). HepG2 cells were grown in humidified 37° C. incubators at 5% v/v $CO_2$.

Example 8

Preparation of HBV/Baculovirus Transfer Vector with Specific Point Mutations The recombinant HBV/baculovirus system used for antiviral testing has been previously described (Delaney et al., *Antimicrob Agents Chemother* 45(6): 1705-1013, 2001). In brief, the recombinant transfer vector was created by excising a fragment containing the 1.3×HBV genome construct and cloning it into the multiple cloning region of a baculovirus vector pBlueBac4.5 (Invitrogen, Carlsbad, Calif.). Point mutations were created by site directed mutagenesis using the commercial kits according to the manufacturers specifications (QuikChange, Stratagene). The nucleotide sequence of the plasmid and the point mutations generated by site directed mutagenesis were confirmed by sequencing using the ABI Prism Big Dye Terminator Cycle Sequencing Ready Reaction Kit according to the manufacturer's specifications (Perkin Elmer, Cetus Norwalk, Conn.). The panel of HBV mutants was generated from a wild type (WT) genotype D HBV isolate by site-directed mutagenesis. Mutants encoded either WT HBV polymerase or polymerase with the amino acid substitutions listed in Table 8 in an HBeAg negative (precore [PC] G1896A mutant) background. Other HBV mutants can be made and tested for antiviral sensitivity in a similar manner.

Example 9

Generation of Recombinant Baculoviruses Containing the 1.3 HBV Construct

Purified recombinant transfer vector and linear AcMNPV baculovirus DNA were co-transfected into Sf21 cells using the BacNBlue transfection kit from Invitrogen (Carlsbad, Calif.); recombinant viruses were isolated by plaque assay according to the manufacturer's instructions. A series of recombinant viruses were amplified from isolated plaques by infecting 100-mm dishes of Sf21 cells. Viral DNA was extracted from amplified viruses using standard procedures. Purified viral DNA was digested with restriction enzymes and then fractionated by electrophoresis in a 1% v/v agarose gel. Southern blotting was performed to determine which virus isolates contained the intact 1.3 HBV construct. A Boehringer Mannheim Random Prime DNA Labeling kit (Indianapolis, Ind.) was used to generate $[P^{32}]$-radiolabeled probes. A full-length double-stranded HBV genome was used as a template for all radiolabeled probes. Viral DNA sequence was confirmed by PCR amplification and sequencing of the polymerase catalytic region.

Example 10

Preparative Baculovirus Amplification and Purification

Baculoviruses were amplified by infecting suspension cultures of Sf21 cells in log phase at a multiplicity of infection (moi) of 0.5 pfu/cell. Infections were allowed to proceed until a majority of the cells in the flasks showed visible signs of infection (four to five days). Virions were concentrated from infected Sf21 medium by centrifugation at 80,000×g and purified through a 20-60% w/v sucrose gradient. Purified virus was titrated in quadruplicate in Sf21 cells by end-point dilution. An aliquot of each high titer stock was used for DNA extraction. The polymerase gene was amplified and sequenced to confirm the presence of the site-directed mutagenesis.

Example 11

Infection (ie., Transduction) of HepG2 Cells with Recombinant HBV Expressing Baculovirus with Antiviral Agents HepG2 cells were seeded at approximately 20-40% confluency and then were grown for 16-24 hours before infection. On the day of infection, triplicate plates of cells were trypsinized, and viable cell number was determined with a hemocytometer using Trypan blue exclusion. Average cell counts were calculated and used to determine the volume of high-titer viral stock necessary to infect cells at the indicated moi. HepG2 cells were washed one time with serum-free MEM to remove traces of serum. Baculovirus was diluted into MEM without serum to achieve the appropriate moi using volumes of 1.0, 0.5, and 0.25 ml to infect 100-mm, 60 mm, and 35-mm dishes, respectively. Baculovirus was adsorbed to HepG2 cells for one hour at 37° C. with gentle rocking every 15 minutes to ensure that the inoculum was evenly distributed. The inoculum was then aspirated and HepG2 cells were washed two times with phosphate-buffered saline and refed MEM-FBS with or without various concentrations of agents.

Replicate HepG2 cell cultures were transduced with WT or mutant HBV by means of baculovirus vectors, and then exposed continuously to different concentrations of each drug 7 days. For each assay, five different concentrations of each drug were tested in duplicate. Drug concentrations for nucleoside analogs (LMV, FTC, L-dT and ETV) were (in nM) 1, 10, 100, 1,000 and 10,000. For the nucleotide analogs (ADV and TFV) concentrations used were 100, 500, 1,000, 5000 and 10,000 nM. Duplicate untreated cultures served as controls. After 7 days culture, DNA was extracted and analysed.

Example 12

Analysis of Secreted HBV Antigen

Detection of hepatitis be antigen (HBeAg) was performed by radioimmunoassay and microparticle enzyme immunoassay using kits purchased from Abbott Laboratories (Abbott Park, Ill., USA). Medium from HepG2 cells was collected, centrifuged at 6,000 g to remove cellular debris, transferred to clean tubes, and stored at 20° C. until analysis. HBeAg values are expressed as fold of positive control. Medium samples were diluted appropriately so that radioimmunoassay results were below positive control values for HBeAg.

Example 13

Detection of Intracellular Replicative Intermediates

HBV core particles were isolated from the cytoplasmic fraction of HepG2 cells lysed in 0.5% w/v NP-40. Cytoplasmic extracts were adjusted to 10 mmol/l McC12 and unprotected DNA was removed by an incubation to 500 g/ml Proteinase K for 1.5 hours at 37° C. HBV DNA in the samples was then extracted using commercial DNA extraction kits such as Qiagen (DNA extraction) or in-house methods using sequential phenol and chloroform extractions, and the nucleic acids were recovered by ethanol precipitation. Nucleic acids were resuspended in 50 μl/1 TE (10 mmol/l Tris, 1 mmol/l ethylenediaminetetraacetic acid), normalized by OD260, and digested with 100 g/ml RNase (Boehringer Mannheim, Indianapolis, Ind.) for one hour at 37° C. before analysis by real-time PCR or electrophoresis and Southern blotting using a full length [$^{32}$P]-labelled HBV and autoradiographed with the aid of Bio-Rad phosphorimaging screens. Images were recorded and analysed using a Bio-Rad Model FX Molecular Imager equipped with "Quantity One" software.

The amount of HBV DNA in drug-treated cells was expressed as a fraction of the mean amount of HBV DNA in untreated controls, defined as 1.0 based on image densities. Pairs of values from duplicates were averaged to give a single value for each of three independent assays, from which means and standard deviations were calculated. The resulting data were analysed using TableCurve2D, which generated dose-response plots from which EC50, EC90 and AUC (area under curve) were estimated.

Example 14

Antiviral Testing Performed with Wild-Type and HBV/Baculovirus Encoding Polymerase Mutations The effect of the antiviral agents on the panel of mutants is shown in Table 9. Antiviral testing shows that the mutations previously selected on ETV at codons 184 and 202 in association with the LMV resistant mutants also affect sensitivity to ADV and TDF. The 184 and 202 mutations were selected by patients on ADV treatment alone (see patients A, and B). HBV encoding other mutations will be tested using similar methodology.

Example 15

Clonal Analysis of HBV Polymerase Mutants Selected During Antiviral Therapy

Clonal analysis was performed at the time of the virological breakthrough on LMV and ADV therapy to determine if multiple HBV mutations are on the same genome for patient D. The catalytic domains of the reverse transcriptase/polymerase were amplified separately using primers OS1 and OS2 (refer to Example 4) sequenced as previously described Ayres et al., 2004 in supra). The OS1/OS2 PCR products obtained from these samples were cloned into PCRScript Amp SK+ (Stratagene) as per the manufacturers instructions. PCR amplification was carried out directly from each clone and the PCR product was sequenced for each sample as above, using the OS1/OS2 PCR primers as sequencing primers. During failure of ADV monotherapy, the patient previously selected rtN236T and rtA181T. At the time of dual ADV and LMV resistance the mutation profile detected by amplification of the entire genome and direct sequencing included rtN53D, rtS116P, rtD134V, rtN139E, rtA181V, rtI233V, rtN236T, rtM250L. The rtN236T and the rtA181T were detected in 100% of clones. Two major clonal profiles were detected: rtN139E+rtQ149K+rtM250L+rtI233V in 55% of clones and rtS85A+rtN139K+rtN238D in 45% of the clones, respectively. The key mutation at rtS85A and the mutations at rtN139E/K and rtQ149K were not detected by direct sequencing in the initial amplification of the HBV genome and PCR sequencing but was detected by directed sequencing of the clones and also the PCR product used for clonal analysis.

The rtM250L mutation could affect sensitivity to entecavir as previously another mutation at codon rt250 was selected during ETV treatment. The rtI233V is located in a similar position in a sequence alignment with the HIV reverse transcriptase to the HIV codon 215 (Batholomeusz et al., *Antivir Ther.* 9(2):149-6, 2004) The rtM204I/V+/−rtL180M LMV resistance mutations were not detected in the clonal analysis at the time of virological breakthrough on combination ADV and LMV therapy.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 4

Patient A HBV Polymerase and envelope mutations detected during ADV therapy

| Treatment | HBV RT Mutations | HBsAg Mutations |
|---|---|---|
| LMV | rtM132L | sT189I/T |
| Pre ADV | rtL/M180M | sL/P192L |
|  | rtA/V200A | sT195T/I |
|  | M/I204M | sW/L196L |
| ADV | rtN53K | sT45K |
|  | rtY54D | sL175F |
|  | rtL180M | sI195M |
|  | rtT184T/S |  |
|  | rtA200A/V |  |
|  | rtM204M/I/V |  |
| ADV | rtN53K | sT45K |
| (Sample A) | rtY54D | sL175F |
|  | rtL180M | sI195M |
|  | rtT184S |  |
|  | rtM204V |  |
| ADV | rtN53K/N | sT45K |
| (Sample B) | rtL180M | sL173L/F |
|  | rtT181A/V |  |
|  | rtN236T |  |

TABLE 5

Patient B RT and Polymerase mutations detected during ADV therapy

| Treatment | HBV RT Mutations | HBsAg Mutations |
|---|---|---|
| ADV | rtY124H | sT118A |
|  | rtH126R, | sP120T |
|  | rtT128N | sP127A |
|  | rtS135C, | sI195M |
|  | rtL180M |  |
|  | rtS202C, |  |
|  | rtM204V |  |
|  | rtH248N |  |

TABLE 6

Patient C RT and Polymerase mutations detected during ADV therapy

| Treatment | HBV RT Mutations | HBsAg Mutations |
|---|---|---|
| ADV | rtI16T | sT114P |
|  | rtI53V | sI195M |
|  | rtS54T | sS204N |
|  | rtN122T | sI208T |
|  | rtM145L | sS210R |
|  | rtL180M |  |
|  | rtM204V |  |
|  | rtM250L~ |  |

TABLE 7

Patient D RT and Polymerase mutations detected by direct PCR amplification sequencing during ADV and LMV therapy*

| Treatment | HBV RT Mutations | HBsAg Mutations |
|---|---|---|
| ADV and LMV | rtN53D, | sL173F |
|  | rtS116P, | sS204G, |
|  | rtD134V, | sS210R |
|  | rtL180M, |  |
|  | rtA181V, |  |
|  | rtN238D |  |
| ADV AND LMV* | rtN53D, | sV14A, |
| (1946 days since start | rtS116P, | sG130R, |
| of initial therapy) | rtD134V, | sM133T, |
|  | rtN139E, | sW172L, |
|  | rtA181V | sS204G, |
|  | rtS219A, | sS210R |
|  | rtI233V, |  |
|  | rtN236T, |  |
|  | rtM250L |  |

*In the clonal analysis the key mutation at rtS85A, and other mutations at rtN139K/E and rtQ149K were also detected as minor species.

TABLE 8

Description of HBV Mutants

| Code for | Reverse transcriptase (rt) amino acid residue number | | | | | | |
|---|---|---|---|---|---|---|---|
| HBV mutants | 169 | 173 | 180 | 184 | 202 | 204 | 250 |
| WT | I | V | L | T | S | M | M |
| L180M double | I | V | M | T | S | V | M |
| L180M quad | I | V | M | G | I | V | M |
| V173L triple | I | L | M | T | S | V | M |

TABLE 9

Antiviral Results Summary

| Polymerase Change | | LMV | FTC | ADV | TFV | ETV | L-dT |
|---|---|---|---|---|---|---|---|
| none | EC50 | 1.0 | 1.0 | 1.0 | 1.0 | 1.0 | 1.0 |
| (WT) | EC90 | 1.0 | 1.0 | 1.0 | 1.0 | 1.0 | 1.0 |
|  | AUC | 1.0 | 1.0 | 1.0 | 1.0 | 1.0 | 1.0 |
| L180M | EC50 | >4,000 | >1,370 | 2.9 | 2.3 | 70.0 | 4.7 |
| double | EC90 | >435 | >263 | 1.5 | 2.6 | >12,048 | >41 |
|  | AUC | 353.1 | 761.4 | 1.7 | 2.1 | 215.9 | 13.7 |
| L180M | EC50 | >4,000 | >1,370 | 1.8 | 6.9 | 366.7 | 31.5 |
| quad | EC90 | >435 | >263 | 2.9 | 5.2 | >12,048 | >41 |
|  | AUC | 603.4 | 464.4 | 1.3 | 4.2 | 242.7 | 21.1 |
| V173L | EC50 | >4,000 | >1,370 | 0.8 | 1.5 | 7.0 | 42.7 |
| triple | EC90 | >435 | >263 | 0.9 | 2.9 | 79.5 | >41 |
|  | AUC | 625.3 | 1200.0 | 0.4 | 2.3 | 47.5 | 12.7 |

BIBLIOGRAPHY

Allen et al., *Hepatology* 27(6): 1670-1677, 1998
Angus et al., *Gastroenterology.* 125(2):292-7. 2003
Aye et al., *J. Hepatol.* 26: 1148-1153, 1997
Ayres et al., *Methods Mol. Med.* 2004; 95:125-49.
Bartholomeusz et al., *Intervirology* 40(5-6): 337-342 1997
Batholomeusz et al., *Antivir Ther.* 9(2):149-62004
Benhamou et al., *Lancet* 358: 718-723, 2001
Benzaria et al., *J Med. Chem.* 39: 4958-4965, 1996
Boyd et al., *Antiviral Chem. Chemother.* 32: 358-363, 1987
Calio et al., *Antiviral Res.* 23: 77-89, 1994
Das et al., *J. Virol.* 75(10): 4771-4779, 2001
(Delaney et al., *Antimicrob Agents Chemother* 45(6). 1705-1013, 2001).
Dienstag et al., *New England J Med* 333: 1657-1661, 1995
Frick et al., *Antimicrob. Agents Chemother.* 37: 2285-2292, 1993
Gaillard et al., *Antimicrob Agents Chemother.* 46(4): 1005-1013, 2002
Gilson et al., *J Viral Hepat* 6: 387-395, 1999
Heathcote et al., *Hepatology* 28. A620, 1998
Hendricks et al., *Am J Clin Pathol* 104: 537-46, 1995
Kruger et al., Hepatology 22: 219A, 1994
Main et al., *J. Viral Hepatitis* 3: 211-215, 1996
Norder et al., (*J. Gen. Virol.* 74: 341-1348, 1993
Perrillo et al., *Hepatology* 32: 129-134, 2000
Peters et al., *Transplantation* 68: 1912-1914, 1999
Price et al., *Proc. Natl. Acad. Sci. USA* 86(21): 8541-8544, 1989
Ren and Nassal, *J. Virol.* 75(3): 1104-1116, 2001
Severini et al., *Antimicrobial Agents Chemother.* 39: 430-435, 1995
Stuyver et al., *Hepatology* 33: 751-757, 2001
Summers and Mason, *Cell* 29: 403-415, 1982
Suo et al., *J Biol. Chem.* 273(42): 27250-27258. 1998
Vere Hodge, *Antiviral Chem Chemother* 4: 67-84, 1993
Xiong et al., *Hepatology.* 28(6): 1669-73, 1998
Ying et al., *J Viral Hepat.* 7(2): 161-165, 2000

What is claimed is:

1. A method for determining whether an HBV strain exhibits reduced sensitivity to a nucleoside or nucleotide analog said method comprising isolating DNA or corresponding mRNA from the HBV and screening for a combination of mutations in the nucleotide sequence encoding the DNA polymerase resulting in the following substitution of the amino acid sequence of the DNA polymerase at all of rtN53K, rtL180M, rtN236T, and rtA181V, wherein the foregoing amino acid positions are numbered in reference to the M of the YMDD motif of the HBV DNA polymerase being position 204 and wherein said combination of mutations is indicative of a variant that exhibits a decreased sensitivity to one or more nucleoside or nucleotide analogs.

2. The method of claim 1 wherein the nucleotide analog is Adefovir.

3. The method of claim 1 wherein the nucleotide analogs are Adefovir and Lamivudine.

* * * * *